(12) United States Patent
Wright

(10) Patent No.: US 10,322,424 B2
(45) Date of Patent: Jun. 18, 2019

(54) ELECTROSTATIC FLUID DELIVERY BACKPACK SYSTEM

(71) Applicant: Victory Innovations Company, St. Louis Park, MN (US)

(72) Inventor: Clifford Wright, San Diego, CA (US)

(73) Assignee: Victory Innovations Company, St. Louis Park, MN (US)

( * ) Notice: Subject to any disclaimer, the term of this patent is extended or adjusted under 35 U.S.C. 154(b) by 0 days.

(21) Appl. No.: 15/831,017

(22) Filed: Dec. 4, 2017

(65) Prior Publication Data

US 2018/0085765 A1     Mar. 29, 2018

Related U.S. Application Data

(63) Continuation of application No. 15/387,319, filed on Dec. 21, 2016.
(Continued)

(51) Int. Cl.
| | |
|---|---|
| *B05B 5/03* | (2006.01) |
| *B05B 5/16* | (2006.01) |
| *A61L 2/22* | (2006.01) |
| *B05B 5/053* | (2006.01) |
| *B05B 7/08* | (2006.01) |
| *B05B 7/24* | (2006.01) |
| *B05B 9/08* | (2006.01) |
| *B05B 15/656* | (2018.01) |

(Continued)

(52) U.S. Cl.
CPC .............. *B05B 5/03* (2013.01); *A61L 2/22* (2013.01); *B05B 5/0533* (2013.01); *B05B 5/1691* (2013.01); *B05B 7/0892* (2013.01); *B05B 7/2475* (2013.01); *B05B 9/0861* (2013.01); *B05B 12/002* (2013.01); *B05B 15/62* (2018.02); *B05B 15/65* (2018.02); *B05B 15/656* (2018.02); *A61L 2202/11* (2013.01); *A61L 2202/15* (2013.01); *B05B 7/2416* (2013.01)

(58) Field of Classification Search
CPC ....... B05B 5/03; B05B 5/0533; B05B 5/1691; B05B 15/62; B05B 15/65; B05B 15/656; B05B 7/0892; B05B 7/2475; B05B 7/2416; B05B 12/002
USPC ...................................................... 239/696
See application file for complete search history.

(56) References Cited

U.S. PATENT DOCUMENTS

| | | |
|---|---|---|
| 3,630,441 A | 12/1971 | Felici et al. |
| 3,740,612 A | 6/1973 | Gauthier et al. |
| (Continued) | | |

FOREIGN PATENT DOCUMENTS

| | | |
|---|---|---|
| CN | 1036343 A | 10/1989 |
| CN | 1962855 A | 5/2007 |
| (Continued) | | |

*Primary Examiner* — Jason J Boeckmann
(74) *Attorney, Agent, or Firm* — Mintz Levin Cohn Ferris Glovsky and Popeo, P.C.

(57) ABSTRACT

An electrostatic fluid delivery system is configured to deliver fluid, such as a disinfectant fluid, onto a surface by electrically charging the fluid and forming the fluid into a mist, fog, plume, or spray that can be directed onto a surface, such as a surface to be cleaned. The system atomizes the fluid using a high-pressure air stream and passes the fluid through an electrode inside a nozzle assembly to charge, such as negatively charge, droplets of the atomized fluid. The system uses a unique nozzle design that is configured to optimally atomize the fluid into various sized droplets.

15 Claims, 51 Drawing Sheets

US 10,322,424 B2
Page 2

Related U.S. Application Data

(60) Provisional application No. 62/383,108, filed on Sep. 2, 2016, provisional application No. 62/270,430, filed on Dec. 21, 2015.

(51) Int. Cl.
    *B05B 15/62* (2018.01)
    *B05B 15/65* (2018.01)
    *B05B 12/00* (2018.01)

(56) References Cited

U.S. PATENT DOCUMENTS

| | | |
|---|---|---|
| 4,358,059 A | 11/1982 | Coffee |
| 4,576,827 A | 3/1986 | Hastings et al. |
| 4,583,694 A | 4/1986 | Williams et al. |
| 4,848,660 A | 7/1989 | O'Connell |
| 5,121,884 A | 6/1992 | Noakes |
| 5,405,090 A | 4/1995 | Greene et al. |
| 5,501,400 A | 3/1996 | Kuo |
| 5,538,190 A | 7/1996 | Greene et al. |
| 5,779,162 A | 7/1998 | Noakes et al. |
| 5,932,011 A | 8/1999 | Noakes et al. |
| 5,984,199 A | 11/1999 | Restive |
| 6,216,966 B1 | 4/2001 | Prendergast et al. |
| 6,311,903 B1 | 11/2001 | Gaw et al. |
| 6,682,004 B2 | 1/2004 | Kadlubowski et al. |
| 6,708,908 B2 | 3/2004 | Heldt et al. |
| 6,866,212 B2 | 3/2005 | Sumiyoshi et al. |
| 7,007,826 B2 | 3/2006 | Shapanus et al. |
| 7,114,670 B2 | 10/2006 | Robidoux |
| 7,152,817 B2 | 12/2006 | Wilson et al. |
| 7,159,797 B1 * | 1/2007 | Lammers ............... B05B 15/65 239/394 |
| 7,182,280 B2 | 2/2007 | Ye et al. |
| D608,856 S | 1/2010 | Dammkoehler |
| D622,500 S | 8/2010 | Pho |
| 7,784,718 B2 * | 8/2010 | Ohno ................. B05B 5/03 239/291 |
| 7,823,808 B2 | 11/2010 | Yamaguchi et al. |
| 7,823,809 B2 | 11/2010 | Yamaguchi et al. |
| 7,841,549 B2 | 11/2010 | Yamaguchi et al. |
| 7,997,511 B2 | 8/2011 | Reynolds et al. |
| D654,567 S | 2/2012 | Yamamoto et al. |
| 8,322,631 B2 | 12/2012 | Richardson et al. |
| 8,465,263 B2 | 6/2013 | Jones et al. |
| 8,496,194 B2 | 7/2013 | Baltz |
| 8,596,555 B2 | 12/2013 | Thompson et al. |
| 8,746,585 B2 | 6/2014 | Harwood et al. |
| 8,807,455 B2 | 8/2014 | Havlovitz et al. |
| 8,813,867 B2 | 8/2014 | Peterson et al. |
| 8,893,990 B2 | 11/2014 | Seitz et al. |
| D720,039 S | 12/2014 | Tinius |
| 9,016,599 B2 | 4/2015 | Johnson et al. |
| D731,027 S | 6/2015 | Sanz Perez |
| 9,085,008 B2 | 7/2015 | Kinne et al. |
| 9,149,109 B2 | 10/2015 | Slaton |
| 9,192,952 B2 | 11/2015 | Becker et al. |
| D749,192 S | 2/2016 | Fontaine |
| 9,259,748 B2 | 2/2016 | Pirrie |
| D757,214 S | 5/2016 | Richter et al. |
| D770,015 S | 10/2016 | Wright |
| 9,475,073 B2 | 10/2016 | Kinne et al. |
| 9,517,479 B2 | 12/2016 | Hines et al. |
| 9,604,234 B2 | 3/2017 | Thompson et al. |
| 9,604,235 B2 | 3/2017 | Thompson et al. |
| D818,701 S | 5/2018 | Wright |
| 2003/0006321 A1 | 1/2003 | Mather |
| 2003/0205631 A1 | 11/2003 | Barron et al. |
| 2005/0039738 A1 | 2/2005 | Zimlich et al. |
| 2007/0048452 A1 | 3/2007 | Feng et al. |
| 2007/0194157 A1 | 8/2007 | Golden et al. |
| 2008/0105763 A1 * | 5/2008 | Fahy ................. B05B 11/0018 239/373 |
| 2008/0213499 A1 * | 9/2008 | Matsumoto ............... B05B 5/03 427/483 |
| 2009/0026293 A1 | 1/2009 | Yamada et al. |
| 2010/0147700 A1 * | 6/2010 | Field ................. A47L 11/4083 205/687 |
| 2012/0018478 A1 | 1/2012 | Hanna et al. |
| 2014/0110493 A1 | 4/2014 | Cooper |
| 2014/0158787 A1 | 6/2014 | Chen et al. |
| 2015/0314312 A1 | 11/2015 | Luczak et al. |
| 2015/0321215 A1 | 11/2015 | Huh et al. |
| 2017/0173607 A1 | 6/2017 | Wright |
| 2017/0291181 A1 | 10/2017 | Wright |

FOREIGN PATENT DOCUMENTS

| | | |
|---|---|---|
| CN | 103611206 A | 3/2014 |
| EP | 0315615 A2 | 5/1989 |
| EP | 1 832 349 A1 | 9/2007 |
| RU | 39839 U1 | 8/2004 |
| SU | 1826928 C | 7/1993 |
| WO | WO-2014/055432 A1 | 4/2014 |
| WO | WO-2016/037074 A1 | 3/2016 |

* cited by examiner

ELECTROSTATIC FLUID DELIVERY BACKPACK SYSTEM

CROSS REFERENCE TO RELATED APPLICATIONS

The present application is a Continuation of U.S. application Ser. No. 15/387,319 filed Dec. 21, 2016, entitled ELECTROSTATIC FLUID DELIVERY BACKPACK SYSTEM and claims priority under 35 U.S.C. § 119 to U.S. Provisional Application Ser. No. 62/270,430, filed Dec. 21, 2015, entitled ELECTROSTATIC FLUID DELIVERY BACKPACK SYSTEM, and U.S. Provisional Application Ser. No. 62/383,108, filed Sep. 2, 2016, entitled ELECTROSTATIC FLUID DELIVERY BACKPACK SYSTEM, the disclosures of which are incorporated herein by reference.

BACKGROUND

Infectious disease is too often acquired in places that should be safe, such as ambulances, hospitals, schools, restaurants, hotels, athletic facilities, and other public areas. These places are traditionally cleaned by spraying a fluid disinfectant onto surfaces and wiping down the surface with a cloth. Unfortunately, such cleaning methods have been shown to be ineffective.

An improved mechanism for spraying down surfaces uses an electrostatic delivery system that sprays an electrically charged fluid, such as a disinfectant, onto surfaces. In an electrostatic delivery system, a fluid such as chemical solution is atomized by a high-pressure air stream as it passes through an electrode inside a nozzle. Negatively charged particles are thereby induced onto droplet surfaces of the solution to form electric field charge within the spray plume of the solution. The electrostatic charge causes the fluid to cling to a surface to increase the likelihood that the disinfectant will cover and clean the surface. However, existing electrostatic delivery systems are unwieldy and inconvenient due to the power requirements of such systems. They are typically tethered to an electric cord or powered by air compressor or natural gas, which makes the system heavy. In addition, they are expensive. Cost and cording remain the two main obstacles to widespread adoption. In many cases existing corded products prohibit or restrict their use in applications where an extension cord is cumbersome, inconvenient, slow, and in some cases creating a safety concern by introducing a potentially dangerous tripping hazard.

In view of the foregoing, there is a need for improved electrostatic fluid delivery system.

SUMMARY

Disclosed herein is an electrostatic fluid delivery system that is configured to deliver fluid, such as a disinfectant fluid, onto a surface by electrically charging the fluid and forming the fluid into a mist, fog, plume, or spray that can be directed onto a surface, such as a surface to be cleaned. The system atomizes the fluid using a high-pressure air (or other gas) stream and passes the fluid through an electrode inside a nozzle assembly to charge, such as negatively charge, droplets of the atomized fluid. The system uses a unique nozzle design that is configured to optimally atomize the fluid into various sized droplets. In addition, the system is powered by a DC (direct current) power system rather than an AC (alternating current) system to eliminate cumbersome power cords. In an embodiment, the DC power system includes a lithium ion battery. The device can electrically or positively charge a liquid or gas. In another embodiment, any of the systems described herein is powered by AC power source or any other type of power source including, for example, a solar power source. The system can also use, for example, an alternator or a Tesla coil.

In one aspect, there is disclosed an electrostatic sprayer device, comprising: a housing; an electrostatic module inside the housing; a reservoir having a cavity adapted to contain a fluid; at least one nozzle fluidly connected to the reservoir wherein the nozzles emit fluid in a direction along a flow pathway; a pump that propels fluid from the reservoir to the at least one nozzle; a direct current battery that powers at least one of the electrostatic module and the pump; an electrode assembly that electrostatically charges the fluid, wherein the electrode assembly is at least one of: (1) a first electrode assembly formed of a plurality electrodes electrically attached to the electrostatic module, wherein each electrode emits ions along an axis that is parallel to the flow pathway of the fluid emitted from the nozzle such that the plurality electrodes form a static electrical field through which the fluid passes; and (2) a second electrode assembly formed of a tube that fluidly through which fluid flows from the reservoir toward the at least one nozzle, wherein at least a conductive portion of the tube is electrically attached to the electrostatic module, and wherein the conductive portion of the tube physically contacts the fluid as it flows through the tube and applies an electrical charge to the fluid.

Other features and advantages should be apparent from the following description of various embodiments, which illustrate, by way of example, the principles of the disclosure.

BRIEF DESCRIPTION OF THE DRAWINGS

FIG. 1 shows a perspective view of an electrostatic fogger device.

FIG. 2 shows an exploded view of the device of FIG. 1.

FIG. 3 shows an enlarged view of a nozzle assembly of the device.

FIG. 4 shows a close up view of a nozzle surrounded by a charging ring.

FIGS. 5 and 6 show a backpack style fogger.

FIG. 7 shows an embodiment of a handheld fogger.

FIG. 8 shows another embodiment of a handheld fogger.

FIG. 9 shows another embodiment of an electrostatic fogger device.

FIG. 10 shows the device of FIG. 9 with a portion of an outer housing removed.

FIG. 11 shows a nozzle assembly of the device.

FIG. 12 shows a nozzle assembly of the device with a nozzle tool attached thereto.

FIG. 13 shows a nozzle housing of the nozzle assembly.

FIG. 14 shows a nozzle component with nozzles.

FIG. 15 shows an electrode assembly.

FIG. 16 shows an electrode.

FIG. 17 shows a perspective view of the nozzle tool.

FIG. 18 shows an enlarged view of a handle region of the system.

FIG. 19 shows an enlarged view of a handle region of the system with a portion of the outer housing removed.

FIG. 20 shows an interior of a cap of a liquid or fluid reservoir of the system.

FIG. 21 shows a perspective view of the reservoir.

FIG. 22 shows a perspective view of the system with the reservoir removed.

FIG. 23 shows an exemplary embodiment of the pump of the system.

FIG. 24 shows an ion tube isolator that provides a positive or negative electrical charge to fluid flowing the tube isolator via direct contact with the fluid.

FIGS. 25A-26 show various views of a backpack style electrostatic fluid delivery system.

FIG. 44B shows a cross-sectional view of the system with the pump off.

FIG. 44C shows the system with the pump powered on.

DETAILED DESCRIPTION

Before the present subject matter is further described, it is to be understood that this subject matter described herein is not limited to particular embodiments described, as such may of course vary. It is also to be understood that the terminology used herein is for the purpose of describing a particular embodiment or embodiments only, and is not intended to be limiting. Unless defined otherwise, all technical terms used herein have the same meaning as commonly understood by one skilled in the art to which this subject matter belongs.

Disclosed herein is an electrostatic fluid delivery system that is configured to deliver fluid, such as a disinfectant fluid, onto a surface by electrically charging the fluid and forming the fluid into a mist, fog, plume, or spray that can be directed onto a surface, such as a surface to be cleaned. The system atomizes the fluid using a high-pressure air (or other gas) stream and passes the fluid through an electrode inside a nozzle assembly to charge, such as negatively charge, droplets of the atomized fluid. The system uses a unique nozzle design that is configured to optimally atomize the fluid into various sized droplets. In addition, in a non-limiting embodiment, the system is powered by a DC power system rather than an AC system to eliminate cumbersome power cords. In an embodiment, the DC power system includes a lithium ion battery. The device can electrically or positively charge a liquid or gas.

The system is configured to electrostatically charge the atomized fluid via direct charging, induction charging, indirect charging, or any combinations thereof. In the case of direct charging, fluid flows through an electrically conductive tube or other conduit that is electrostatically charged such that the fluid contacts the tube and is charged by direct contact with the tube, as describe below. For induction or indirect charging, the fluid is passed through a medium, such as air, that has been electrostatically charged by one or more electrodes or pins that create a static electric field through which the fluid passes to receive c charge. The electrode may or may not be in the fluid stream. In an embodiment, the fluid is charged through both direct contact with the charged tube and by flowing the fluid through a medium such as air that has been charged with electrodes such as, for example, described herein.

Figure 1:
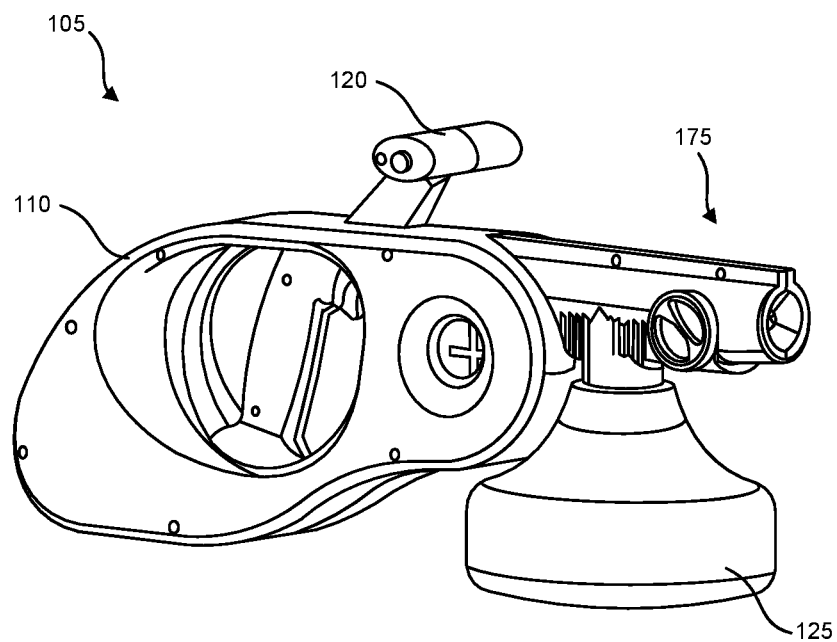

FIG. 1 shows a perspective view of an electrostatic fluid delivery system 105 that is configured to electrically charge and atomize a fluid for spraying onto a surface. The system 105 includes a housing 110 that is sized and shaped to be held by a user. The housing 110 has an ergonomic shape that can be easily grasped and held but it should be appreciated that the size and shape of the housing can vary. In an embodiment, one or more vents or openings are positioned in the outer housing to provide communication between an inside of the outer housing and the outside such as for venting.

The system 105 may have one or more actuators or controls 120 that can be actuated by a user to activate and operate the system. A fluid expelling region 175 is located at a front of the housing 110 and has an opening through which atomized fluid is expelled. The system 105 also includes a reservoir 125 that defines a chamber in which fluid can be stored. The chamber of the reservoir 125 communicates internally with a nozzle assembly 205 (FIG. 2) for supplying fluid to be electrically charged and atomized by the nozzle assembly, as described more fully below.

Figure 2:
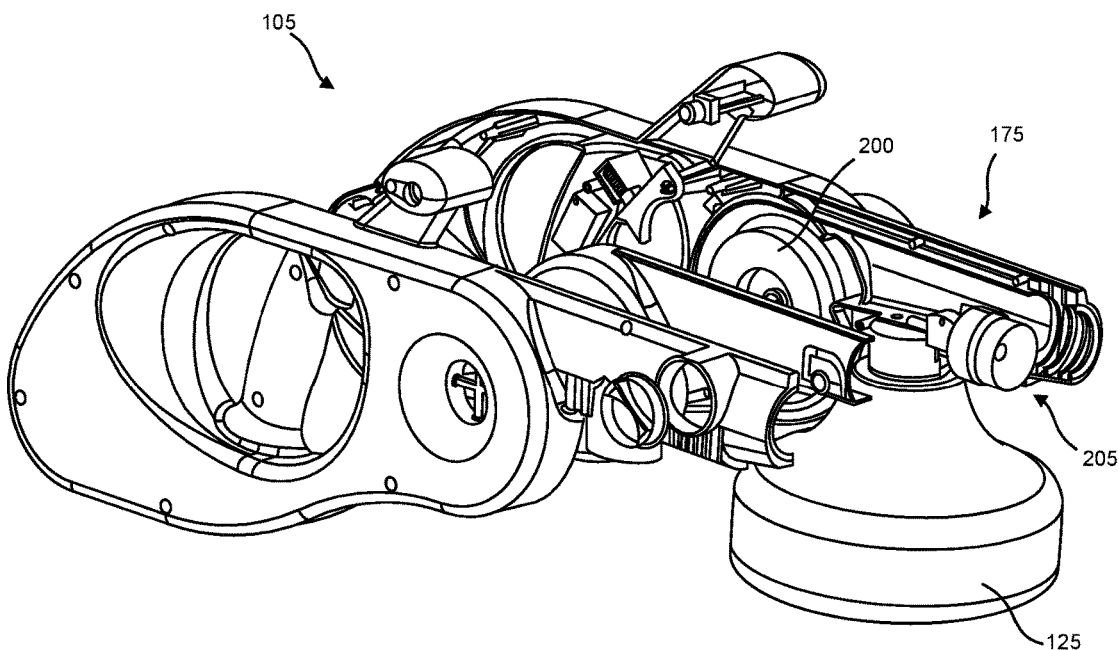
Figure 3:
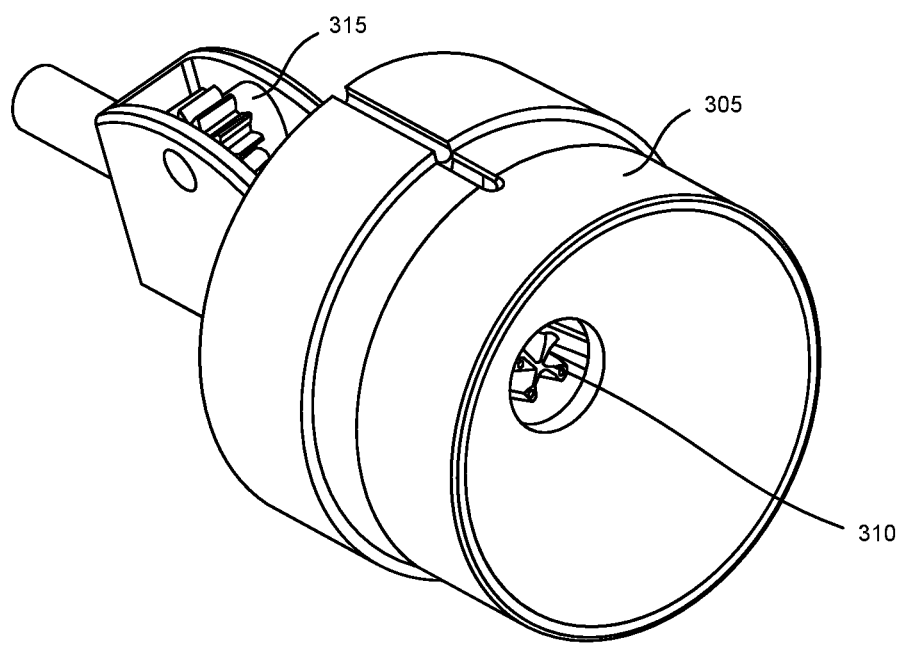
Figure 4:
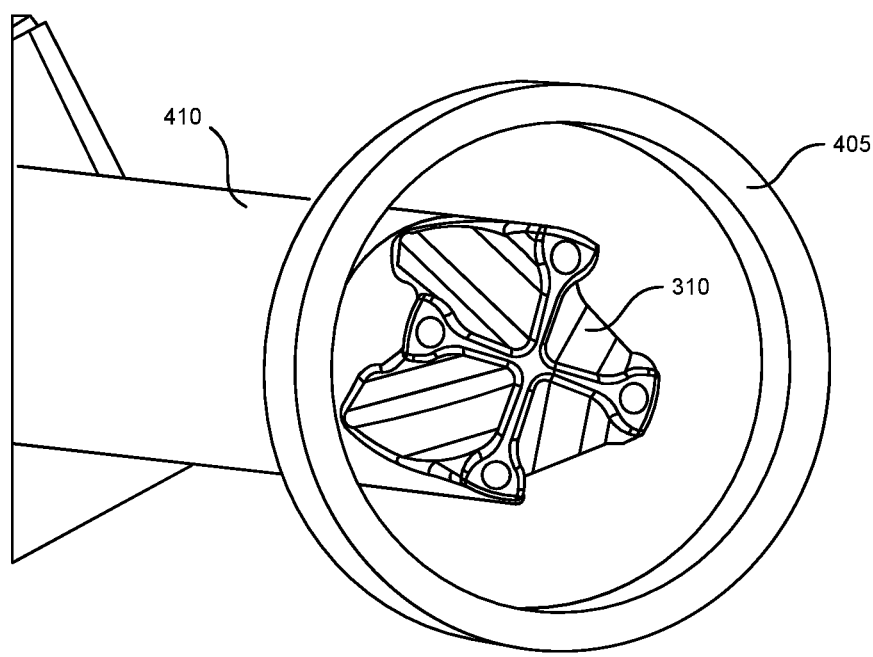
Figures 5, 6:
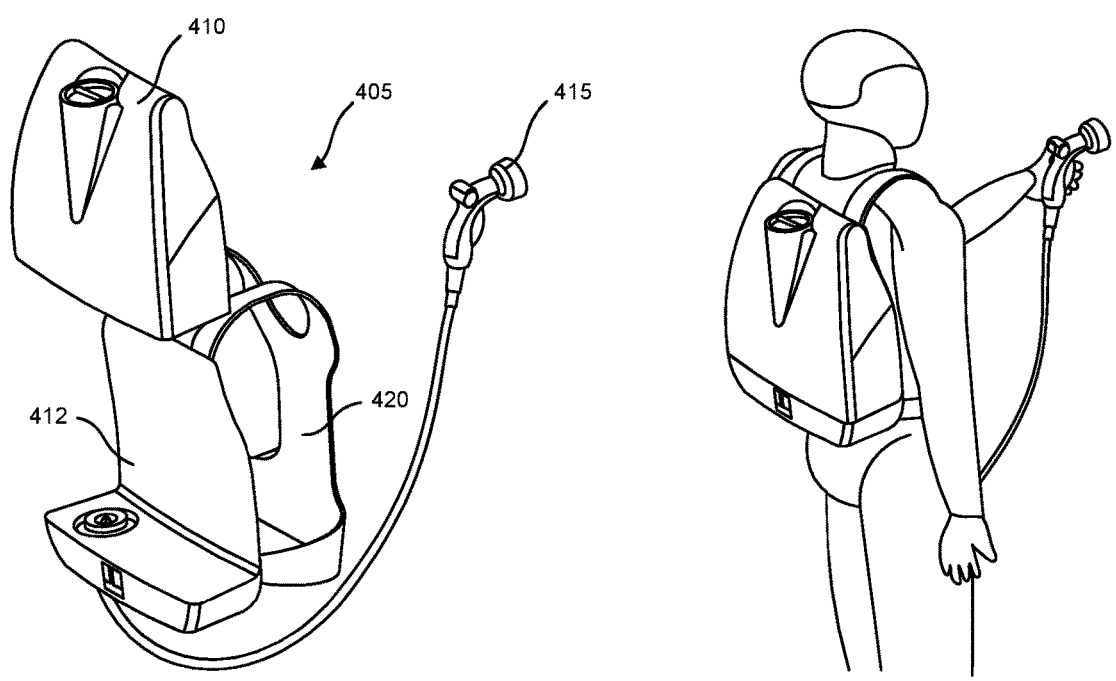
Figure 7:
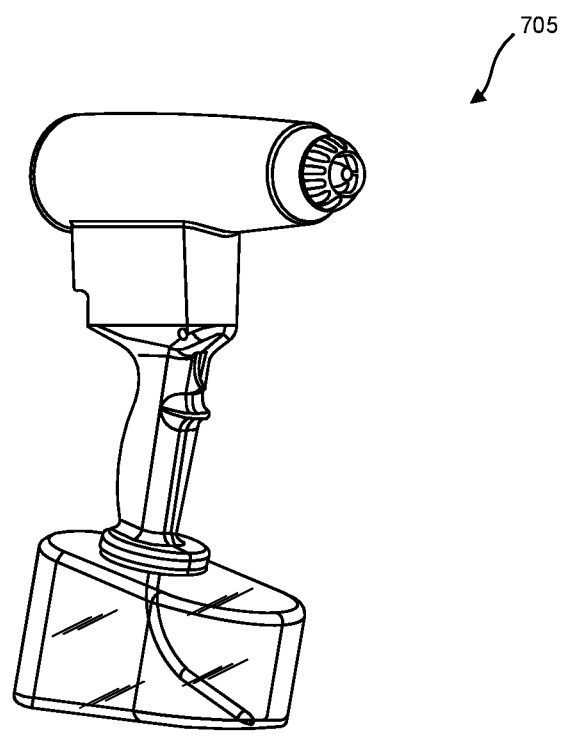
Figure 8:
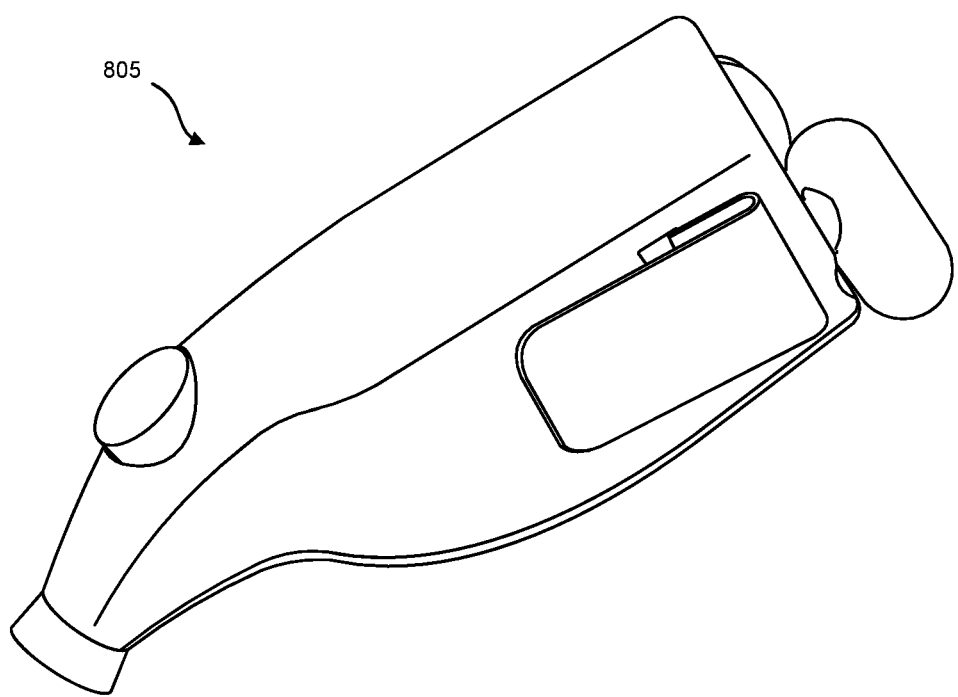

FIG. 2 shows the system 105 in an exploded state. The housing is formed of multiple pieces that connect to contain an inner region in which is housed a fan 200. The fan 200 is powered by a battery, such as a lithium ion battery. An electrical circuit board converts the DC power to AC power for powering the fan. The system may include a stator coupled to the battery as well as a protection circuit module (PCM).

The fan 200 (or a pump) operates to blow fluid (gas or liquid) toward a nozzle assembly 205 in the fluid expelling region 175 of the system. The nozzle assembly 205 atomizes and expels fluid in a spray. As the fan blows air toward the nozzle assembly, it creates a pressure differential that sucks fluid from the reservoir 125 into the nozzle assembly 205 where it is atomized and expelled as a result of the fan 200 blowing air therethrough. It should be appreciated that other mechanisms can be used to blow air or to blow or otherwise propel liquid from the reservoir. In an embodiment, a piston pump is used to deliver air pressure to the nozzle tip. A piston pump can pull from the reservoir tank to push fluid or pressurize straight to the nozzle tip. For a smaller footprint embodiment (such as the embodiments of FIGS. 7 and 8) a Pneumatics Micro Pump can act as a solenoid pulling fluid by a magnetic movement. The device can also include a pump that pulls a vacuum in the reservoir or fluid tank to cause fluid to flow out of the reservoir toward the nozzles(s).

FIG. 3 shows an enlarged view of the nozzle assembly, which includes an annular housing 305 having a central opening in which is positioned a nozzle 310. The housing 305 has a conically or frustoconically shaped surface that can be curved or straight. The surface is shaped such that fluid from the nozzle 310 bounces back and forth along the surface to form a turbulent flow that atomizes the fluid. In an embodiment, the fluid is atomized to droplets in the range of 5 microns to 40 microns in size. The nozzle 310 is mechanically coupled to a drive assembly 315 that moves the nozzle 310 relative to the housing to control the size of the droplets. In this manner, the user can move the nozzle back and forth to achieve a desired plume profile.

FIG. 4 shows an enlarged view of the nozzle 310. The tip of the nozzle 310 is positioned centrally within a charge ring 405 that is positioned within the housing 305 (FIG. 3) in the assembled device. The charge ring 405 is positioned as such (deep inside the housing) to reduce the likelihood of a user touching the charged ring. The charge ring 405 is grounded and also electrically connected to a power source for achieving a positive voltage on the charge ring 405 during use. As the nozzle 310 expels the atomized fluid through the charge ring 405, it positively charges the fluid. In this manner, the electrically charged plume of fluid will cling to surfaces that it is sprayed upon.

With reference still to FIG. 4, the nozzle 310 has a series of openings through which fluid is expelled. The openings communicate with an internal lumen of a tube 410 through which fluid flows from the reservoir 125 (FIG. 1). The openings are arranged in a unique spatial pattern comprised of four openings with each opening positioned 90 degrees away from an adjacent opening so as to form a cross pattern. The openings can vary in size. In an embodiment, the openings are 0.063 inches in diameter. As mentioned, the nozzle can be connected to a drive assembly that varies the position of the nozzle to control the plume profile.

The electrostatic fluid delivery system may vary in size and shape. FIGS. 5 and 6 show a backpack embodiment 405 that is configured to be worn on the back of user. The system includes a fluid tank 410 that is removably mounted to a frame 412 such that the tank 410 can be interchanged with another tank. The frame 412 is connected to a harness 420 or other support for mounting on a user's back, as shown in FIG. 6. The tank 410 is fluidly connected to a handheld nozzle 415 through which a plume of electrically charged fluid is expelled. The backpack embodiment can include any component of the other systems described herein, including the electrostatic configurations and removable reservoir.

In addition, FIG. 7 shows another handheld embodiment 705 having a reservoir at a bottom of the device. FIG. 8 shows an embodiment 805 that has a hand pump that can be pumped to generate a pressure differential that expels a plume of fluid out of the device.

FIG. 9 shows another embodiment of the system 105. As in the previous embodiment, the system 105 has an outer housing 110 that forms a handle that can ergonomically be grasped by a single hand of a user. The system 105 includes at least one actuator that can be actuated to turn on and also turn off an internal pump, as well as a second actuator for turning on and off an electrostatics charger for expelling a plume of electrostatically charged fluid from a fluid expelling region 175 of the system 105. The system 105 has a removable reservoir 125 for storing fluid to be expelled.

The system 105 ejects high voltage ions to the air by means of a plurality of (such as three or more) sharp, detachable high voltage ion discharge electrodes or pins of a predetermined spacing (such as at 120° spacing) from each other on a rim of a nozzle holder (described below with reference to FIG. 14). The high voltage ion discharge electrodes are each positioned along an axis that is in parallel to an axis of a spray nozzle so that the spray and ions are emitted in the same direction and along a parallel axis and therefore the droplets in the spray are surrounded and covered by ion stream and can be efficiently charged when they meet the ion stream. The electrodes thus emit, propel, or otherwise send out ions or charge in a direction parallel to the direct of fluid flow or an average direction of fluid flow from the nozzles.

FIG. 10 shows the system 105 with a portion of the outer housing 110 removed to show internal components of the system 105. The system 105 includes a pump 1005 that is powered by a battery 1010. The pump 1005 is fluidly coupled to fluid within the reservoir 125 such that the pump can cause a pressure differential to draw fluid from the reservoir and into a nozzle assembly 1015, which is described in detail below. The system 105 further includes an electrostatic module that is electrically connected to an electrostatic ring, as described below. The electrostatic module in an example embodiment is a 12 kV electrostatic module and it is configured to electrostatically charge an item, such as the electrodes, ring, and/or tube described below.

In an embodiment, a light 1017 is positioned at a front end of the system 105 in the fluid-expelling region 175 such that the light aims light toward the direction where fluid is expelled. The light may be an LED light, for example. The light can automatically illuminate when any portion of the system is activated. In an example embodiment, LED light has 100 lumens with the light being directly focused on the path of the liquid that is being sprayed out of the sprayer nozzle. The light can be in multiple colors to allow the user to illuminate florescent antimicrobial solutions (infrared light). In another embodiment the light is black light. At least a portion of the light or electrical components of the light may be insulated from contact with the electrically charged field.

FIG. 11 shows a perspective view of the nozzle assembly 1015, which includes a nozzle housing 1105 having an internal cavity that removably contains a nozzle holder or nozzle component 1110 in which one or more nozzles 1115 are positioned. An annular electrostatic ring 1120 is mounted on a forward edge of the nozzle housing 1105. The electrostatic ring 1120 forms an opening through which fluid is expelled from the reservoir and through at least one of the nozzles by virtue of the pump creating a pressure differential. An insulator element, such as a rubber ring 1125 is positioned on the electrostatic ring 1120 to electrically shield it from the outer housing 110 of the system.

There is a metal contact on the high voltage electrostatic ring 1120 that is exposed at a rear part of the electrostatic ring 1120. A high voltage wire from the electrostatic module is soldered or otherwise electrically connected to this metal contact. The soldering point and adjacent exposed metal is completely sealed by epoxy or other insulator to avoid oxidation and leakage of ions from the electrodes. A ground wire from electrostatic module is connected to ground plate. As discussed, the ground wire is embedded in the handle of the sprayer so that it is in contact with the operator during operation. This serves as electrical return loop to complete an electrical circuit. The electrostatic ring is electrically charged so that it transfers the charge to the electrodes that are electrically connected to the ring. In another embodiment, the electrodes themselves are individually connected to the electrostatic module.

Figure 12:
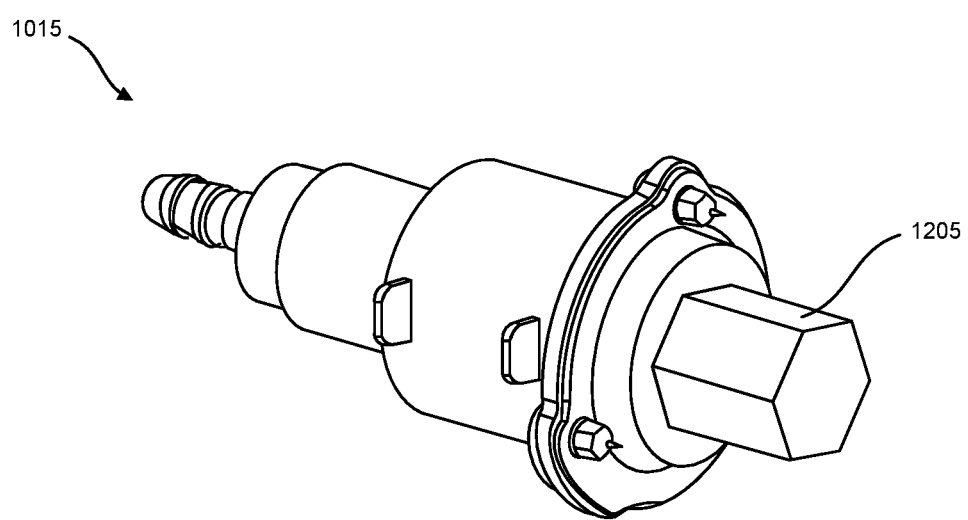

As shown in FIG. 12, the system 105 also includes a nozzle tool 1205 that removably and mechanically couples to the nozzle assembly for manipulating the nozzle component 1110. The nozzle tool 1205 is sized and shaped to be inserted into a front opening in the nozzle housing 1105. When inserted into the nozzle housing 1105, the nozzle tool 1205 mechanically couples to the nozzle component 1110 in a manner that permits the nozzle tool 1205 to lock and/or move the nozzle component 1110 relative to the nozzle housing 1105, as described more fully below.

In an embodiment, the tool 1205 couples to and removes nozzle component by a counter clock turn and by pushing in until nozzle component decouples and can be removed. In this regard, pushing the nozzle component deeper into the housing using the tool causes a threaded portion of the nozzle component to engage a threaded nut or bolt of the housing that secures the nozzle component to the housing. The user can then unthread the nozzle tool and remove it from the housing.

The tool 1205 can also be used to adjust the three-way nozzle by turning it in a desired rotational direction. The user can select three different spray patterns by turning the nozzle component so that a desired nozzle fluidly couples to the reservoir. In this regard, a portion of the tool mechanically attaches to the nozzle component so that it can apply force to the nozzle component and rotate it until a desired nozzle is in a position that is fluidly coupled to a fluid stream from the reservoir. The system may include a mechanism, such as spring and ball, that provides a noise (such as a clicking sound) when a nozzle is in a position to spray fluid.

Figure 17:
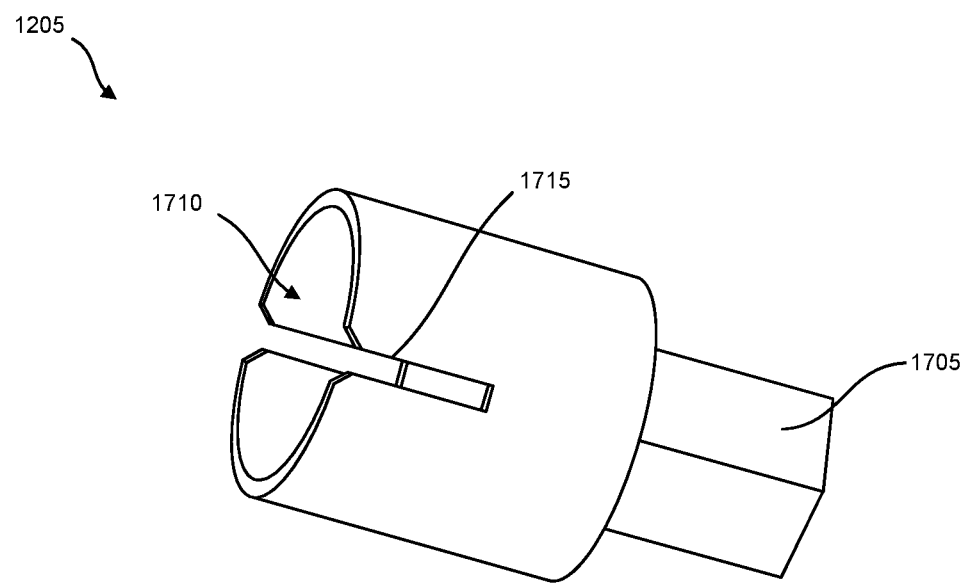

FIG. 17 shows a perspective view of the nozzle tool 1205. The nozzle tool 1205 is sized and shaped to be grasped by a user. It includes a coupler region 1705 that can be removably coupled to a drive device, such as a wrench, or grasped by a user. In an embodiment, the coupler region 1705 is hexagonal shaped so that it can be mechanically coupled to a wrench including a socket wrench. The nozzle tool 1205 includes a cavity or seat 1710 that is size and shaped to receive the outer portion of the nozzle component. For example, the seat 1710 can have a shape that complements and receives the shape of the nozzle component 1110. The nozzle tool 1205 also includes at least one opening 1715 that interlocks with a complementary-shaped protrusion 1405 (FIG. 14) on the nozzle component 1110.

Figure 13:
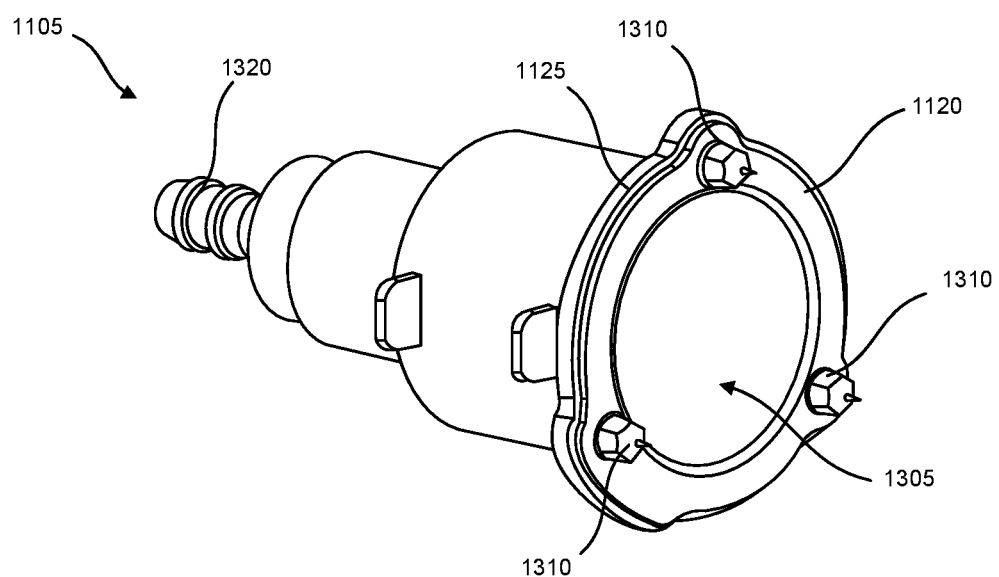

FIG. 13 shows a perspective view of the nozzle housing 1105 without the nozzle component 1110 mounted therein. The nozzle housing 1105 has an elongated, cylindrical shape and defines an internal cavity 1305 sized to removably receive the nozzle component 1110. The electrostatic ring 1120 is mounted at the front edge of the nozzle housing 1105 with the rubber ring 1125 positioned in a seat within the electrostatic ring 1120. The rubber ring 1125 insulates a set of three electrode assemblies 1310 that are mounted on the electrostatic ring 1120 in a predetermined position and orientation. The electrodes assemblies 1310 are arranged around the opening of the nozzle housing 1105 around the nozzles of the nozzle component 1110 when it is positioned in the nozzle housing 1105. In an embodiment, the electrode assemblies 1310 are positioned at 120 degree increments around the electrostatic ring 1120.

The electrostatic ring 1120 includes the three electrodes (which may be made or stainless steel for example) that are electrically isolated by a rubber washer and rubber threaded cap, as described below. The electrostatic ring 1120 that holds electrodes is metal and is built inside of the nozzle housing. The electric static ring is isolated inside a nozzle housing that acts as a protective barrier. The electrostatic ring 1120 contains three internal threaded holes that accept the three electrodes. A rubber washer is inserted between the electrostatic ring 1120 and an insulator on each electrode. The rubber washer aids in tightening of the electrode to the electrostatic ring 1120 and also assists in avoiding leakage of ions from the electrode. The whole electrostatic ring 1120 is isolated inside the nozzle housing so that it acts a protective barrier.

The ring, when properly mounted, forms a safety gap between the discharge electrodes and the outer housing so as to minimize static leakage through the housing. The rubber ring isolates the nozzle housing from causing a charge to the sprayer housing. The rubber ring also isolates the nozzle housing from main body of the sprayer to prevent water from penetrating to a main body of the sprayer.

A hose coupler 1320 is located at an end of the nozzle housing and is configured to be coupled to a house or other conduit that communicates with the reservoir. The hose coupler 132 defines an internal passageway that communicates with the nozzles 1115 for feeding fluid from the reservoir to the nozzles 1115.

Figure 14:
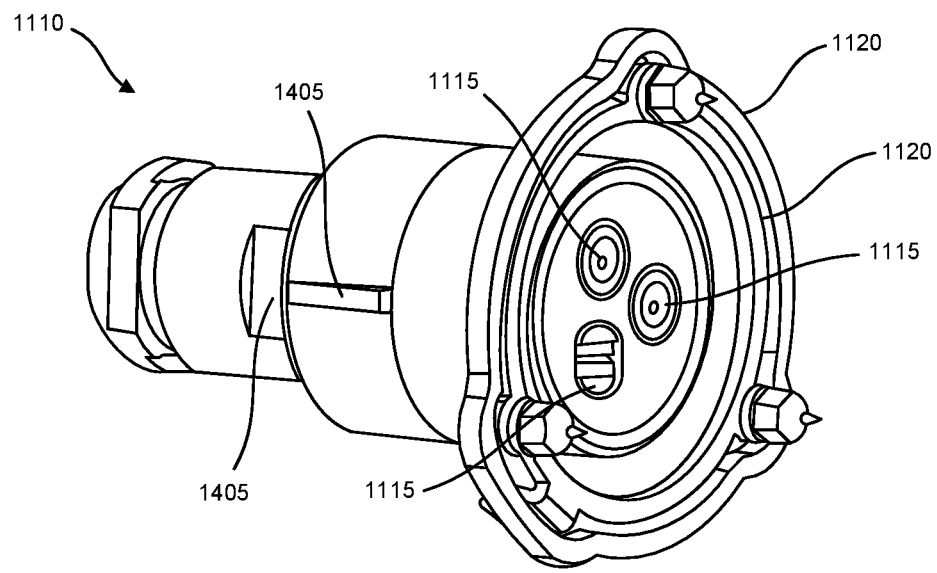

FIG. 14 shows the nozzle component 1110, which is sized and shaped to be removably positioned within the cavity 1305 of the nozzle housing 1105. The nozzle component 1110 houses one or more nozzles 1115, each of which is configured to deliver fluid in a predetermined plume or spray pattern. The nozzle component 1110 includes one or more protrusions 1405 or other structural elements that are sized and shaped to receive complementary structures on the nozzle tool 1205, as described below. Note that the electrostatic ring 1120 with the electrode assemblies 1310 is positioned around the nozzles 1115 with the electrodes of the assemblies 1310 being aligned along an axis that is parallel with an axis of the nozzles.

Any of a variety of nozzle types can be used to achieve a desired flow pattern. There are now described some non-limiting examples of electrodes. In an embodiment, the electrodes include three example types as follows:

(1) A nozzle that provides a cone-shaped spray, with a flow rate of 0.23 L/min, 45° @3.5 bar, SMD=113 um, inner orifice=0.65 mm;

(2) A nozzle that provides a cone-shaped spray, with a flow rate of 0.369 L/min, 60° @3.5 bar, SMD=84 um, inner orifice=0.58 mm;

(3) A nozzle that provides a fan-shaped spray, with a flow rate of 0.42 L/min, 60° @3.5 bar, SMD=100 um, inner orifice=1.00 mm.

It should be appreciated that the aforementioned nozzles are just examples and that variances are within the scope of this disclosure.

Figure 15:
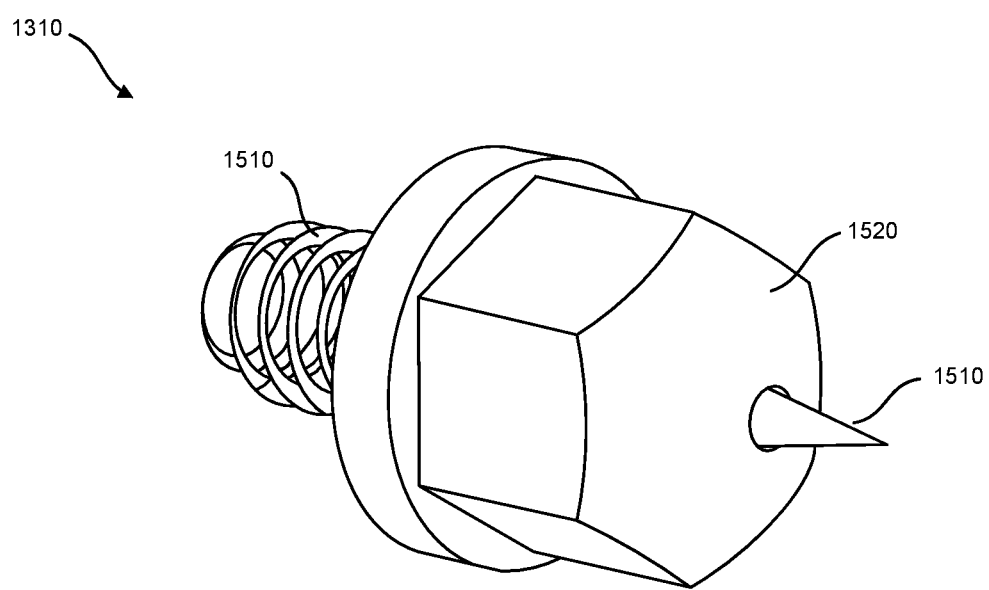
Figure 16:
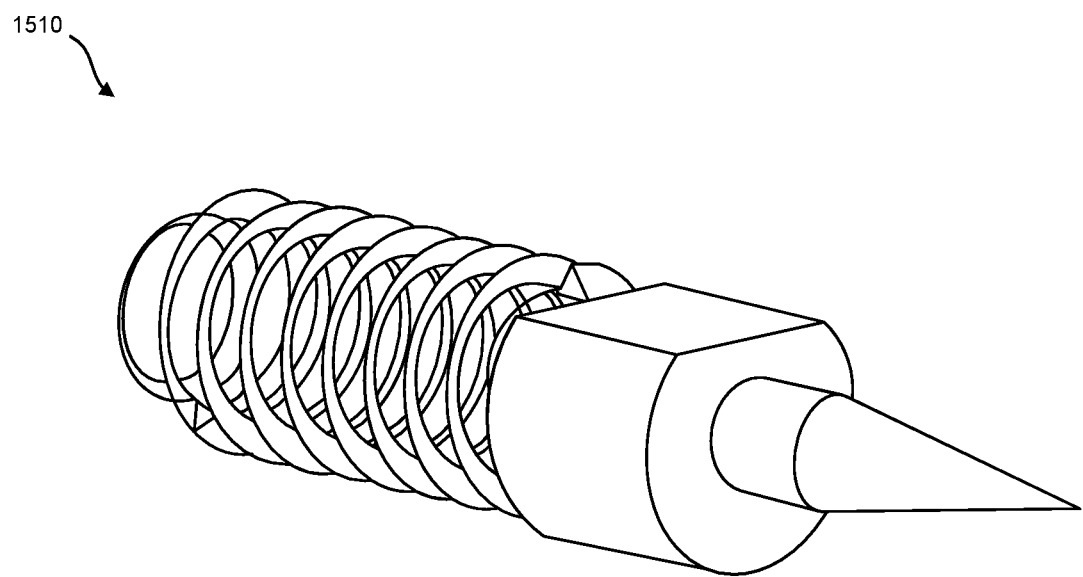

FIG. 15 shows an electrode assembly 1310, which includes a high voltage ion discharge electrode 1510 (or pin) and an insulation element 1520 positioned over the electrode or pin 1510. The insulation element 1520 is sized and shaped so that it covers substantially all of the electrode 1510 and exposes only a front portion of the electrode 1510 in the form of a frontward facing conical tip that is aligned along an axis. FIG. 16 shows the electrode 1510 (sometimes referred to as a pin) without the insulation element 1520. Each high voltage ion discharge electrode in the system has the same structure shown in FIG. 15, a metal pin that is overmolded with plastic at the middle of the pin. Each metal pin has one sharp spike at one end and external screw thread at the other end. The insulation element, which can be plastic, at the middle of pin is for easy gripping during installation and removal, although the pins are not necessarily removable. The plastic is also used to insulate the pin and prevent it from releasing ions from body of pin. The electrode assembly can also be a set of electrode assemblies of the type shown in FIG. 15.

Thus, each electrode assembly 1310 includes an insulator element 1520 that can be formed of a rubber washer that covers a middle section of the electrode, and rubber boot that covers a front section except for a front most, sharpened tip. The rubber washer and a plastic or rubber cap (or boot) isolates the electrode and protects the electrode from static leakage such that only the sharpened tip is exposed and/or uninsulated.

Each high voltage ion discharge electrode is to be screwed into an internal screw thread on the high voltage ring 1120 coupled to the nozzle component 1110. Except for its sharp spike at the end, each high voltage ion discharge electrode is completely covered and concealed by the insulator element after it is installed to the high voltage ring 1120.

Figure 18:
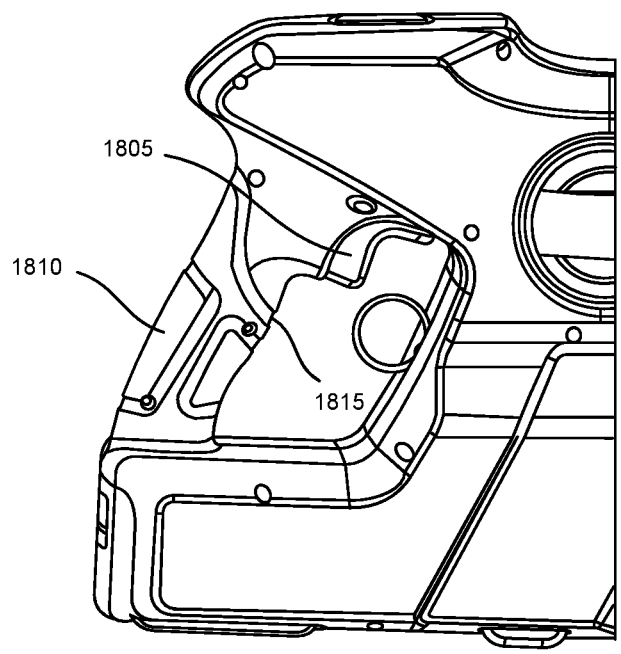

FIG. 18 shows an enlarged view of a handle region of the housing 110. The handle region is ergonomically sized and shaped to be grasped by a single hand of a user. A trigger 1805 or other actuator, such as a knob, switch, etc., is ergonomically positioned so that a user can actuate the trigger with his or her finger when the other fingers are wrapped around a post 1810 of the handle region. A ground wire 1815 or other structure 1815 is embedded into the handle region, such as in the post 1810. The ground wire 1815 is positioned so that it will electrically contact the user's hand when the user grasps the post 1810 during use of the device. In an embodiment, the ground wire is made of copper and is a copper strip of material that contacts the user's hand when the user grasps the device although other materials, such as stainless steel, may be used.

Figure 19:
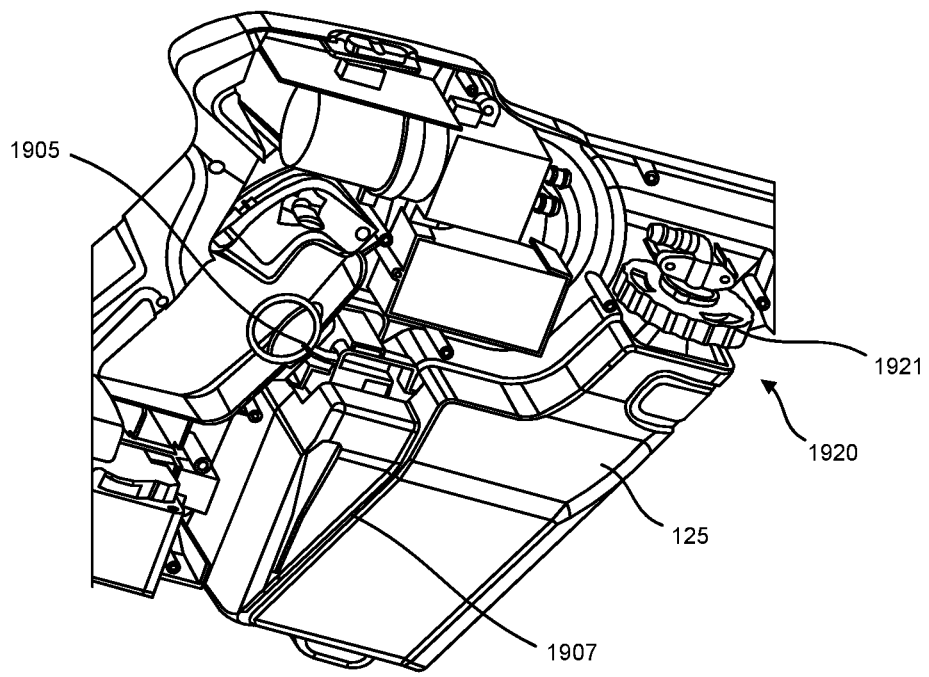

FIG. 19 shows the handle region with a portion of the outer housing 110 removed to show internal components of the device particularly with respect to the reservoir 125, which is a container that encloses an interior cavity that contains fluid. The reservoir is removably attached to the housing 110 and includes a guide surface 1907 that slides into the housing 110. In an embodiment, the guide surface 1907 defines one or more inclined guide projections that interact with the outer housing 110 to properly guide the reservoir 125 into the housing 110.

Figure 20:
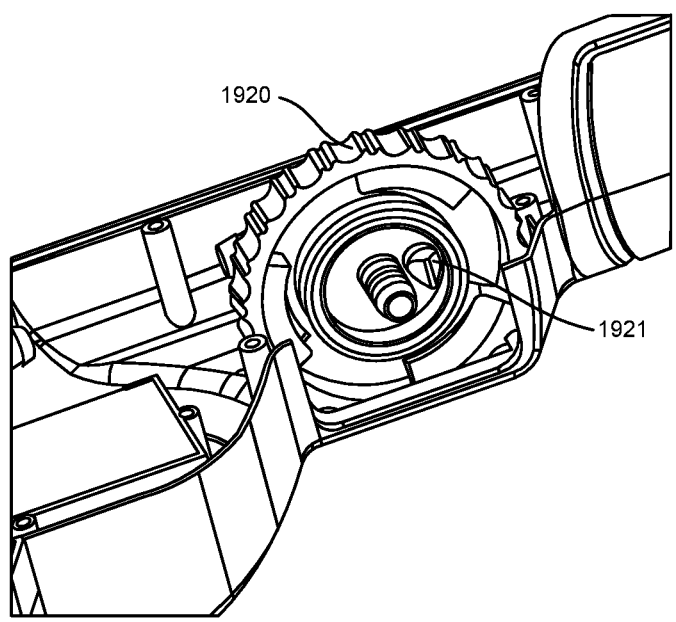

With reference still to FIG. 19, a first detachment mechanism 1905, such as a ring attached to a biased or tensions structure such as a pin, and a second detachment mechanism 1920, such as a rotatable wheel or cap 1921, that can be collectively actuated by a user to enable detachment and locking reattachment of the reservoir 125 to the outer housing. FIG. 20 shows a view of the portion of the cap 1921 that communicates with and covers the interior cavity of the reservoir 125. A one-way valve 2003, such as a duckbill valve, is positioned in the cap 1921 and provides a vent for fluid to enter into the interior of the reservoir from atmosphere as the pump of the system pulls a vacuum in the reservoir.

Figure 21:
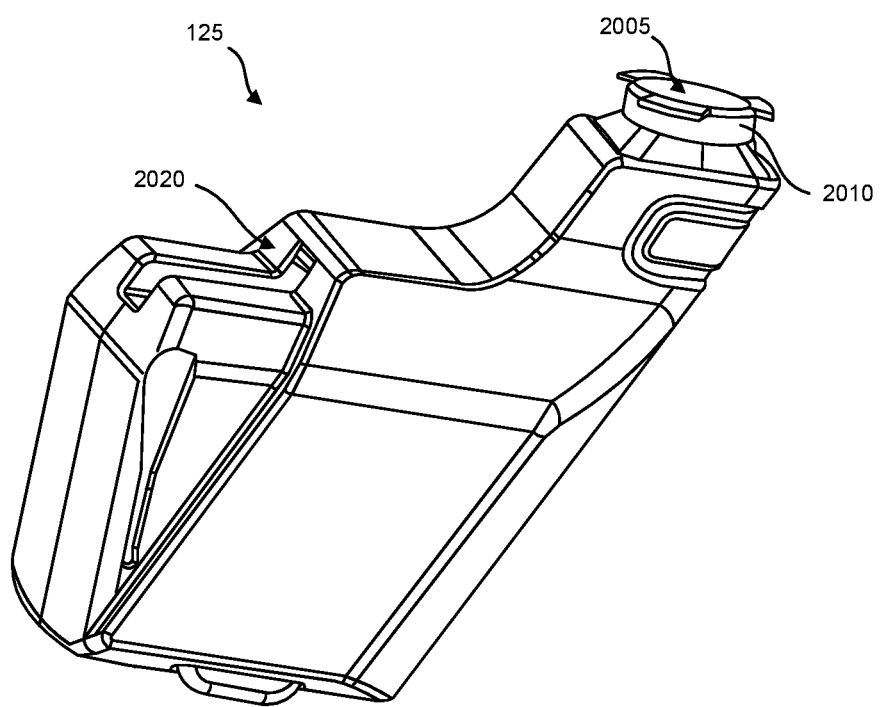

FIG. 21 shows the reservoir 125, which includes an opening 2005 that provides access to the internal cavity of the reservoir 125. The opening 2005 is defined by a neck 2010 having one or more flanges or threads. The neck 2010 sealingly engages the first detachment mechanism 1905 and the second detachment mechanism 1920 of the system for detaching and lockingly attaching the reservoir to the housing.

Figure 22:
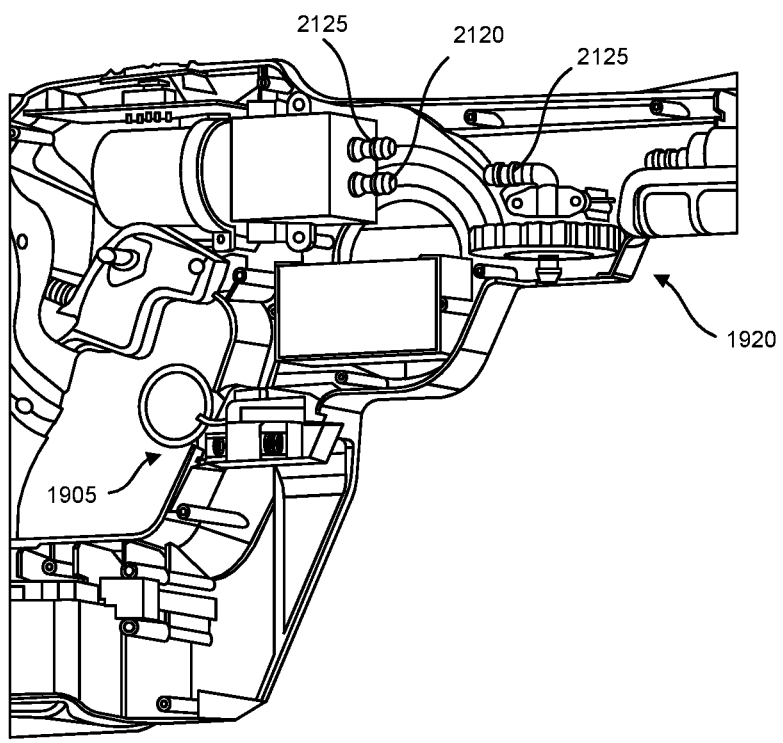

FIG. 22 shows the system with the reservoir 125 and a portion of the outer housing removed. As mentioned, the first detachment mechanism 1905 is configured to attach to the reservoir. Specifically, the first detachment mechanism 1905 includes a spring loaded or tensioned structure that is biased toward locking engagement with a seat 2020 (FIG. 21), structure, or opening in the housing of the reservoir. The first detachment mechanism 1905 is biased to automatically engage and lock with the seat 2020 (or other structure) and lock the reservoir 125 to the housing when it is inserted. In this manner, the detachment mechanism 1905 mechanically prevents the reservoir from being removed from the housing unless the user pulls on, disengages, or otherwise releases the first detachment mechanism 1905 from the reservoir. A user can disengage the first detachment mechanism 1905 from the reservoir by pulling on a structure such as a ring or tab of the first detachment mechanism 1905 to release it from the reservoir. Thus the user must pull out the first detachment mechanism relative to the housing and/or reservoir to release the reservoir from the housing.

With reference still to FIG. 22, second detachment mechanism 1920 is a rotatable structure such as a wheel with threads that engage the neck 2010 (FIG. 21) or a portion thereof of the reservoir 125. In an embodiment, the wheel of the second detachment mechanism 1920 is rotated (such as by a three quarter turn or other turn range) by a user once the reservoir 125 is attached to the outer housing. Rotation of a knob the second detachment mechanism 1920 lockingly and sealingly engages the opening 2005 of the reservoir to the knob and to internal conduits of the system that fluidly couple the fluid in the reservoir to the nozzles.

In this regard, an outlet conduit 2115 fluidly communicates with the internal region of the reservoir when the reservoir is attached and lockingly sealed to the housing. The outlet conduit 2115 can be fluidly attached to a pump inlet conduit 2120 of the pump 1005 such as via a hose (not shown). The pump 1005 has an outlet conduit 2125 that can be fluidly attached to the hose coupler 1320 (FIG. 13) of the nozzle assembly. In this manner, the pump can create a pressure differential that draws fluid from the reservoir and drives it to the nozzle assembly.

Figure 24:
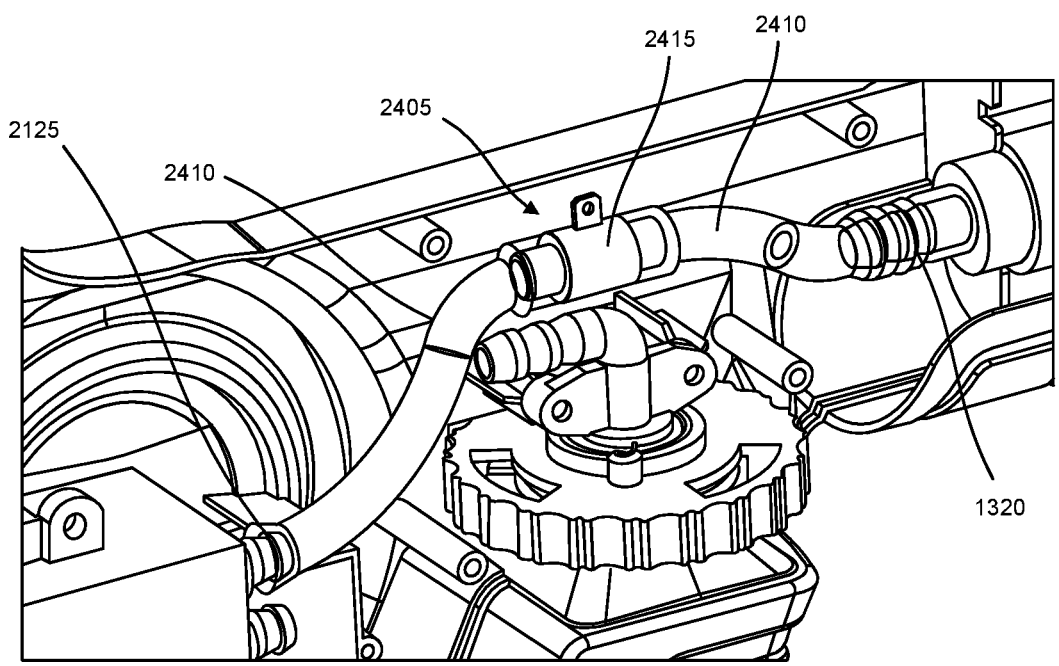

In an embodiment, a hose or tube connects the outlet conduit 2125 of the pump 1005 to the hose coupler 1320 of the nozzle assembly. The tube (or other conduit) that connects the pump 1005 to the nozzle assembly may be configured to electrostatically charge fluid flowing through the tube by direct charging between the tube, which is charged, and the fluid that flows through the tube toward the nozzles. The fluid comes into physical contact with a charged electrode, such as the tube. This is described in more detail with reference to FIG. 24, which shows an ion tube isolator 2405 that electrically charges fluid flowing from the reservoir or pump and toward the nozzles. The ion tube isolator includes the tube 2410 through which fluid passes as well as a high voltage electrode assembly or module 2415 that is electrically connected to the electrostatic module and that is made of a conductive material such as metal. The module 2415 can include a lead where it can be electrically connected to the electrostatic module such as via a conductive wire.

In an embodiment the module 2415 is a conductive material, such as metal. In an embodiment only the module 2415 is conductive and the remainder of the tube 2410 is non-conductive and/or is insulated from contact with any other part of the system. The module 2415 may also be surrounded by an insulator that insulates it from contact with any other part of the system. As fluid flows through the tube 2410, the module 2415 directly contacts the fluid as it flows and passes a charge to the fluid through direct contact with the fluid. In this way, the ion tube isolator 2405 electrostatically charges the fluid prior to the fluid passing through the nozzle.

Since molecules in an aqueous solution are polarized in nature, they can easily carry and conduct electricity from a charge source under high electrical potential (such as a positive electrode in the nozzle holder). Under high electrical potential, the aqueous solution and its path becomes conductive and therefore the charge can be carried to whole liquid system including the hose, pump and tank within the sprayer.

When the aqueous solution is sprayed, the charged solution is forced out through the nozzle and broken up into tiny charged droplets in the air. Because all droplets are carrying the same charge, they will repel each other forming a uniform fine mist in the air. With the help of electrical attraction force between the mist and the intended object, they are pulled like a "magnet" towards the intended object on which opposite charge is induced to its surface via ground. The fine droplets can spread with high mobility and therefore can reach the edges and even backside of an intended object to achieve the desired 360 degree coverage, which is sometimes referred to as a "wrap around effect."

As unlike charges attract each other, theoretically, a positive electrostatic sprayer works the same way as negative electrostatic sprayer. A negative electrostatic module can also be used in place of a positive electrostatic module. In such a case, the droplets sprayed out carry a negative charge and positive charge will be induced on the intended object via ground to attract the negative charges droplets. The negative charge on the droplets will eventually be neutralized by induced positive charge on the intended object when it hit the surface of the intended object.

Although the sprayer can be powered by a DC battery, it can still "pump" electrical charges to the aqueous solution by means of the electrostatic module inside the sprayer. For electrically balanced system, opposite charge may be supplied to compensate the charge spent to the liquid system. This is effectively achieved by means of the ground plate on the handle grip, opposite charge can flow through the ground plate from user to electrostatic module to counterbalance the charge lose to the liquid system.

Figure 23:
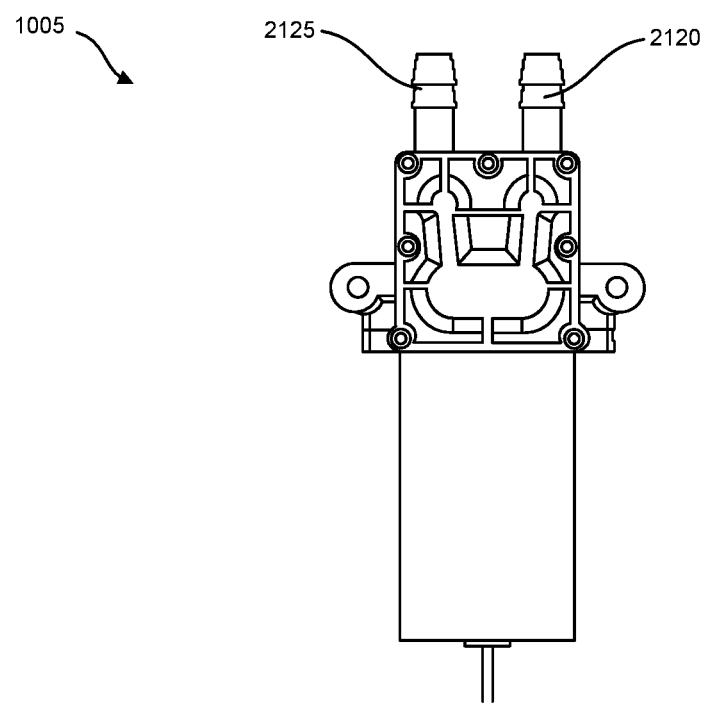

In an embodiment, the pump 1005 is a direct current (DC) pump although an AC pump or any other type of pump can be used as well. The pump includes a rotary motion motor with a connecting rod that drives a diaphragm in an up and down motion when activated. In the process of the downward movement of the diaphragm, a pump cavity creates a pressure differential such as by pulling a vacuum relative to the interior of the reservoir to suck fluid through the pump inlet conduit 2120 from the reservoir. Upward movement of the diaphragm pushes fluid of the pump cavity press through the pump outlet conduit 2125 toward the hose coupler 1320 of the nozzle assembly via an attachment hose that attaches the pump outlet conduit 2125 to the hose coupler 1320. Any mechanical transmission parts and the pump cavity are isolated by the diaphragm within the pump. The diaphragm pump does not need oil for auxiliary lubricating, in the process of transmission, extraction and compression of the fluid. FIG. 23 shows an exemplary embodiment of the pump 1005, which includes the pump inlet conduit 2120 and the pump outlet conduit 2125.

The type of motor used in any of the embodiments described herein can vary. In an embodiment, the system uses a constant speed motor such that the speed of the motor when in use is not vary based upon the remaining power and the battery. This constant speed ability can be achieved by a motor circuit or other electrical element positioned between the battery and the motor. The motor circuit intercepts and monitors the phase changing frequency and adjust the frequency or otherwise regulates the power signal to maintain a constant speed for the motor during operation. This constant speed of the motor has several advantages over variable speed motor including the following.

In a variable speed motor, the motor speed of the motor can vary based upon the motor input voltage. Thus, a higher input voltage result in a higher motor speed. This results in a variation in the output pressure of the pump as the charge in the battery varies, and the output pressure depends on motor speed. A fully charged battery that provides a higher input voltage to the motor can drive the sprayer at highest pressure and so the spray performance is strong. As the battery loses charge, the motor input voltage drops, which results in a reduced motor speed as well as a drop in the pressure the sprayer. As a result, the sprayer performance is reduced. Therefore, inconsistent sprayer performance can result from different levels of battery charge. With constant speed motor as described above, the constant motor speed results in a constant or uniform pressure output from the pump to the spray nozzles, which maintains a consistent sprayer performance that is not based on or independent of the battery voltage.

In an embodiment, the motor operates at a speed of 3000 rpm at 12V. The supplied voltage of the sprayer may be higher than 12V where the nominal voltage of the battery is higher. This can be the case even where a resistor is positioned in series in the power supply line. For example, the nominal voltage of the battery can be 14.8V. The peak speed of the motor (when the battery is fully charged) may attain about 4000 rpm. As higher the motor speed, higher the pump pressure and higher rate of wear which means shorter the pump life.

In use, the user grasps the system 105 and powers the pump so that it propels fluid out of the selected nozzle from the reservoir. As mentioned, the user can use the nozzle tool 1205 to both insert and lock the nozzle assembly 1015 to the system. The user can also use the nozzle tool 1205 to rotate the nozzle component and fluidly couple a selected nozzle to the reservoir. Thus the user can select a desired plume profile for the fluid. The system can also be equipped with just a single nozzle. The user also activates the electrostatic module so that the electrodes become charged and form an electrostatic field in the electrode ring. The fluid is propelled from the nozzle through the ring and through the electrostatic field so that the droplets of fluid in the aerosol plume become positively or negatively electrically charged. As mentioned, the electrodes and the nozzle are aligned along a common parallel axis. This directs the liquid or aerosol toward a desired object based on where the user points the nozzles. In an embodiment, the electrodes do not physically contact the fluid propelled through the nozzles. In another embodiment, the electrodes physically contact the fluid propelled through the nozzles.

Supercharging of Fluid

Figure 44A:
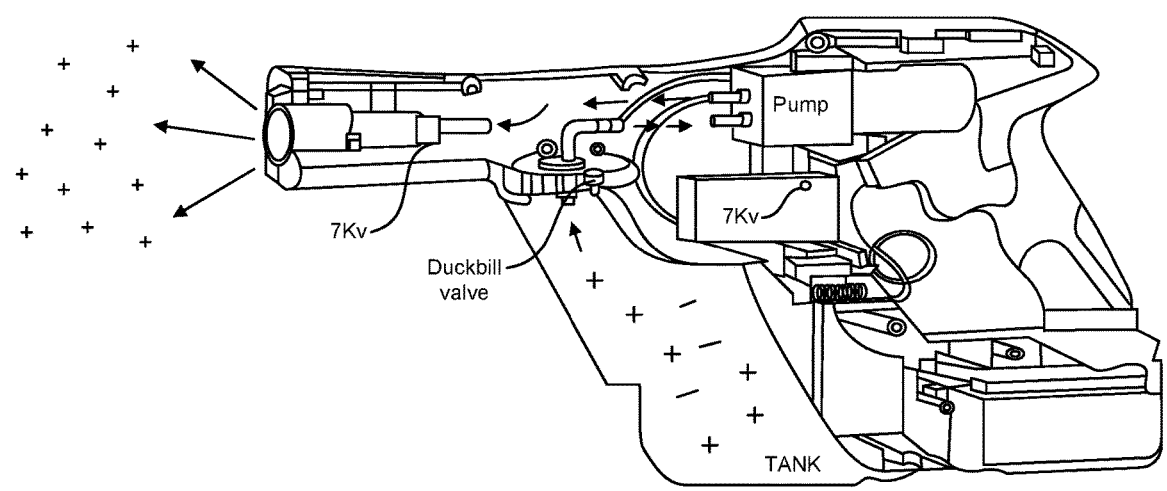
FIG. 44A shows a schematic diagram that illustrates an electrostatic charging process for the system.
Figures 44B, 44C:
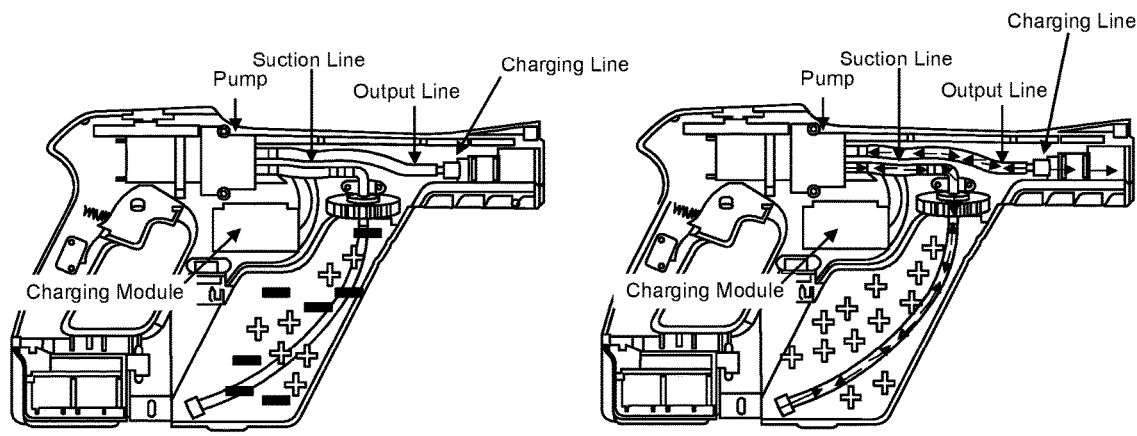

FIG. 44A shows a schematic diagram that illustrates an electrostatic charging process for the system, referred to herein as electrostatic wrapping. As described below, the system is configured to electrostatically charge the fluid at two or more locations thereby resulting in an electrostatically supercharged fluid as the fluid exits the nozzle assembly. The system electrostatically charges the fluid within the reservoir (tank) via the duck bill valve in the upper region of the reservoir. As the fluid passes through the pump and through the electrostatic module, it is charged again at the metal ring of the nozzle assembly. This is described in more detail below.

With reference to FIG. 44A, when a battery is installed inside the device, the user activates the trigger to cause charging of the (7 Kv) electrostatic module. The tank/reservoir has fluid inside. The pump, as mentioned, is a pneumatic piston style pump. The pump causes a pressure differential that opens a valve and starts to vacuum the fluid content out of the tank reservoir. In order for the tank not to collapse, the duck bill valve opens to permit ambient outside air into the tank.

Figure 28:
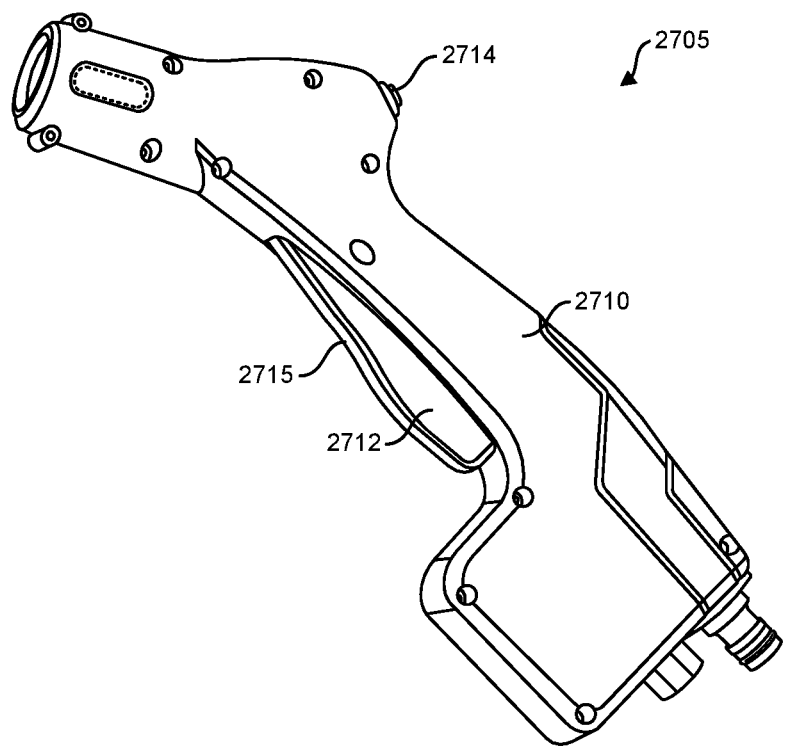
FIG. 28 shows a perspective view of a sprayer.

When the pump opens and the power trigger is activated, the (7 kv module) becomes fully charged. The pump modulates as the pump valves open and close. The electrostatic state is moved between the tank and the nozzle of the device. The charge is a positive charge. When the pump starts to vacuum, the pressure differential propels fluid from the tank through internal fluid conduits until the fluid contacts the nozzle assembly, where the electric static metal or copper ring is fitted inside the nozzle housing.

The fluid is charged going through the nozzle housing in a positive charge. The pump valve opens and closes but so does the outside air, entering only through the duckbill valve, which allows positive and negative ions to inter the tank. This cycle allows the tank to be charged with positive and negative Ions.

When the valve open and allows fluid from the tank to pass through the piston style valve and the fluid hoses of the device, as well as the electric static tubing, the fluid reaches the nozzle assembly, where the fluid becomes supercharged with positive ions. Thus, when the fluid is sprayed at a negatively charged object, the positive ions in the fluid causes the fluid to wrap the negatively charged object, which causes substantial wrapping of fluid around the object.

The double charging process is described in more detail with respect to FIG. 44B and FIG. 44C. FIG. 44B shows a cross-sectional view of the system with the pump off, while FIG. 44C shows the system with the pump powered on. When the pump unit is turned on as shown in FIG. 44B, the electrostatic charge starts at the electrostatic charging ring and works itself back down the fluid output line and suction line, through the pump and into the tank, where the electrostatic charge causes all the ions to be positively charged.

FIG. 44C shows the system with the pump powered on. The pump causes the fluid to move out of the reservoir (tank) and toward the nozzle assembly, which includes the electrostatic ring charging ring. All the positive ions from the tank are pumped from the tank, through the pump, and charged again at the electrostatic charging ring (3720), all prior to becoming atomized by the nozzle assembly. In this manner, the fluid is electrostatically charged at least two times along the fluid flow pathway from the reservoir to the nozzle assembly.

A combination of charging the fluid twice and charging prior to the fluid being atomized at the nozzle assembly enables the system to fully charge the liquid, rather than just charging an outer shell of the atomized particle thereby providing more charged particles. This also provides a greater wrapping effect for the atomized particle and enables the particles to hold the charge longer. The charging process described with respect to FIGS. 44A-44C can be used with any type of power source including AC power source or solar power source, for example, and is not limited to use with a DC power source.

Additional Backpack Embodiment

FIGS. 25A-26 show various views of a backpack style electrostatic fluid delivery system, referred to herein as the backpack system 2405. The backpack system 2405 includes a tank 2410 that is removably mounted on the base 2415. A system of one or more straps 2420 is connected to the base 2415 in a manner that permits the backpack system 2405 to be worn by a user, as shown in FIG. 26. A tubing 2425 extends outward from the backpack system 2405 and is fluidly coupled to the tank 2410, as well as to a handheld sprayer (FIG. 28), as described in detail below. The backpack system 2405 also includes a removable and rechargeable battery 2435, as best shown in FIG. 25. The system can also include vents or openings for permitting heat transfer out of the system.

As shown in FIG. 26, the one or more straps 2420 are positioned and connected to the backpack system 2405 in a manner that permits the backpack system to be worn on the back of a user. The straps 2420 are arranged such that the straps can be positioned around the user's shoulder with the tank 2410 and the base 2415 positioned adjacent the user's back.

FIG. 27 shows the battery system of the backpack system. As mentioned, the battery system includes the battery 2435, which removably attaches to a charger 2605. The charger 2605 has a seat that is sized and shaped to receive the battery 2435. A power cord 2610 extends from the charger 2605 and can be plugged into a power outlet for providing an electrical charge to the charger 2605 and the battery 2435. As mentioned, the battery 2435 can be removably attached to the base 2415 of the backpack system 2405 for providing power to the backpack system 2405. In an embodiment, the charger is a 12 volt charger although this can vary.

As mentioned, the backpack system 2405 includes a handheld sprayer 2705 for spraying electrically charged fluid. FIG. 28 shows a perspective view of the sprayer 2705. The sprayer 2705 is a handheld structure that is sized and shaped to be grasped by a single hand of a user. The sprayer 2705 includes a handle region 2710 that can be grasped within the palm of a user such that the user can wrap his or her fingers around the handle region 2710. A first actuator 2712 is movably mounted on the handle region world 2710 such that a user can actuate the first actuator 2712 such as by squeezing on the first actuator 2712. In an embodiment, the user activates a pump of the backpack system 2405 by pressing on the first actuator 2712 to cause fluid to be expelled out of the sprayer 2705 as described below.

The sprayer 2705 also includes a second actuator 2714 that is ergonomically positioned on the sprayer 2705 such that a user can use a thumb to press on the second actuator 2714 when grasping the sprayer 2705 with his or her fingers. The second actuator 2714 is coupled to a electrostatic charger of the backpack system. The user activates the electrostatic charger by pressing on the second actuator 2714 to electrostatically charge fluid being expelled from the sprayer, as described herein.

With reference still to FIG. 28, is a strip 2715 of conductive material, such as copper, is positioned on the first actuator 2712 such that the strip 2715 will contact the user's hand when the user is grasping the sprayer 2705. Other materials, such as stainless steel, may be used for the strip 2715. The strip, 275 service as an electrical ground connection to the user.

Figure 29:
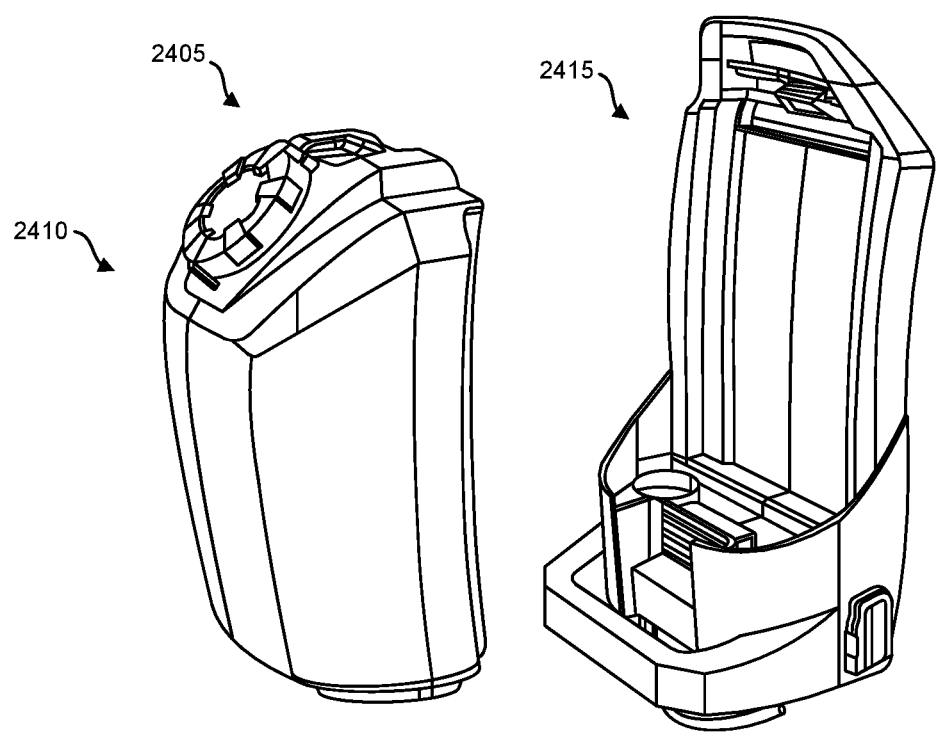
FIG. 29 shows a partially exploded view of the backpack system with the tank detached from the base.

FIG. 29 shows a partially exploded view of the backpack system with the tank detached from the base. The tank 2410 is sized and shaped so that it can fit within a seat of the base 2415. The tank can be shaped so that it can fit within the base 2415 only when positioned in a predetermined orientation relative to the base. The tank 2410 and base 2415 can also include a tongue and groove configuration such that one or more comes in the tank 2410 slidably made with one or more grooves in the base 2415 (or vice versa) to slidably made and secure the tank 2410 to the base 2415.

Figure 30:
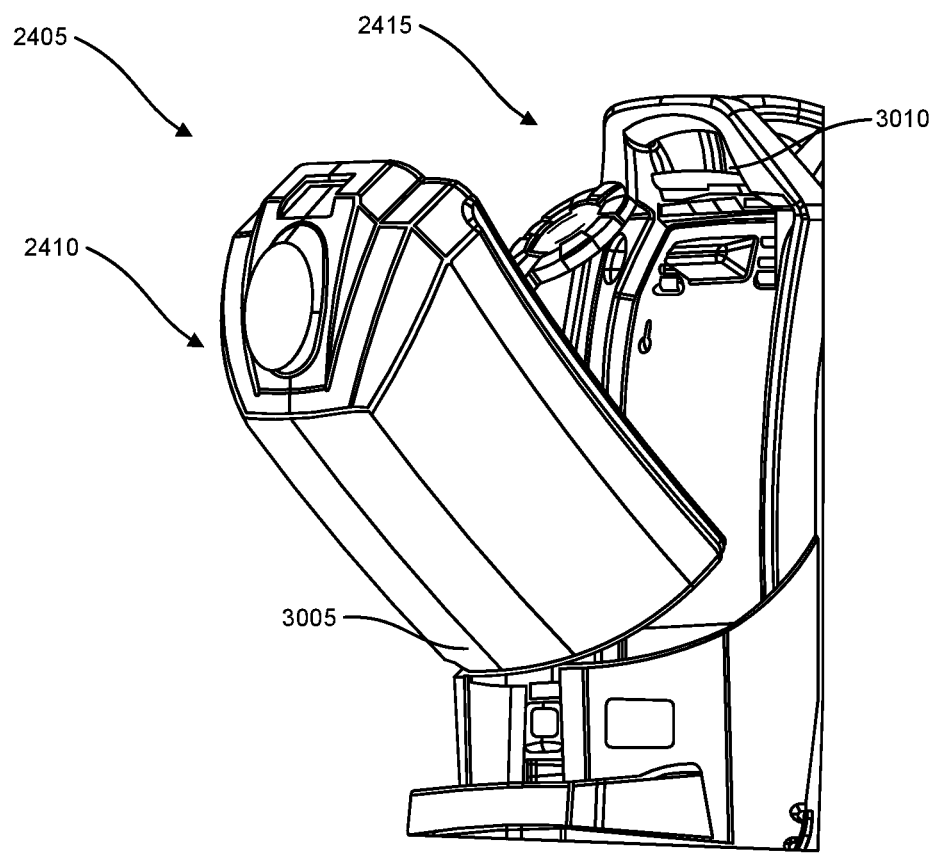
FIG. 30 shows the tank pivoting away from the base.
Figure 31:
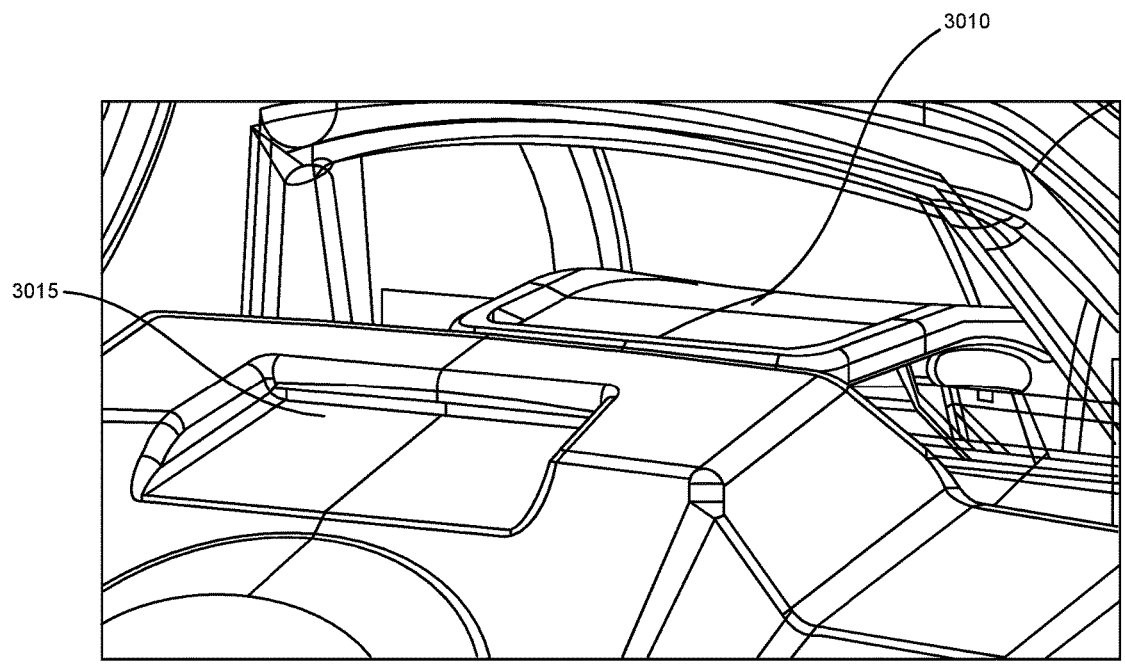
FIG. 31 shows an enlarged view of a hinge that locks the base to the tank.

In an embodiment, the tank 2410 mates with the base 2415 by first hinge hingedly attaching to the base 2415, such as a long the bottom region of the tank 2410. FIG. 30 shows an example of how the tank 2410 can hinge into an attached relationship with the base 2415. The tank 2410 has a bottom attachment region 3005 that is positioned along the seat region of the base 2415. With the tank 2410 positioned as shown in FIG. 30, the user rotates the top region of the tank 2410 toward a locking attachment 3010 the top region of the base 2415. FIG. 31 shows an enlarged view of a hinge that locks the base to the tank. The top region of the tank 2410 includes a cavity 3015 that is sized and shaped to receive the locking attachment 3010 of the base 2415. The locking attachment 3010 is a tongue shaped member or clasp that clasps onto the cavity 3015 to removably secure the tank 2410 to the base 2415.

Figure 32A:
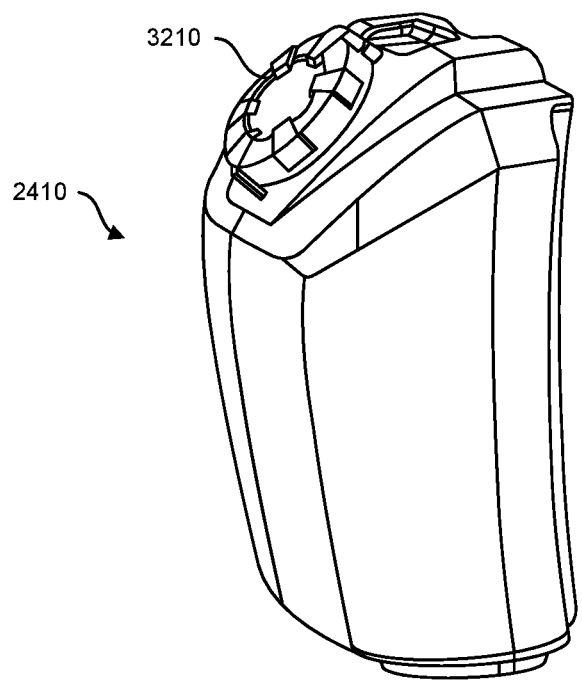
FIG. 32A shows a perspective view of the tank of the backpack system.

FIG. 32A shows a perspective view of the tank of the backpack system. The tank is formed of an outer housing that defines an internal cavity configured to contain a fluid. An opening is located on the tank, such as along an upper top region of the tank. The opening is covered by a cap 3210 that can removably cover the opening into the cavity. The cap, when positioned over the opening, sealingly covers the opening such that fluid inside the cavity is sealed within the cavity of the tank 2410. The tank 2410 removably couples to the base 2415 along the bottom region of the base. In this regard, the tank 2410 includes a valve assembly 3215 (FIG. 32B) that interacts with a corresponding valve assembly 3310 (FIG. 33) in the base to permit fluid to flow from the tank 2410 and into the base 2415, where the fluid can then flow toward the sprayer 2705 via the tubing 2425 (FIG. 24A).

Figure 32B:
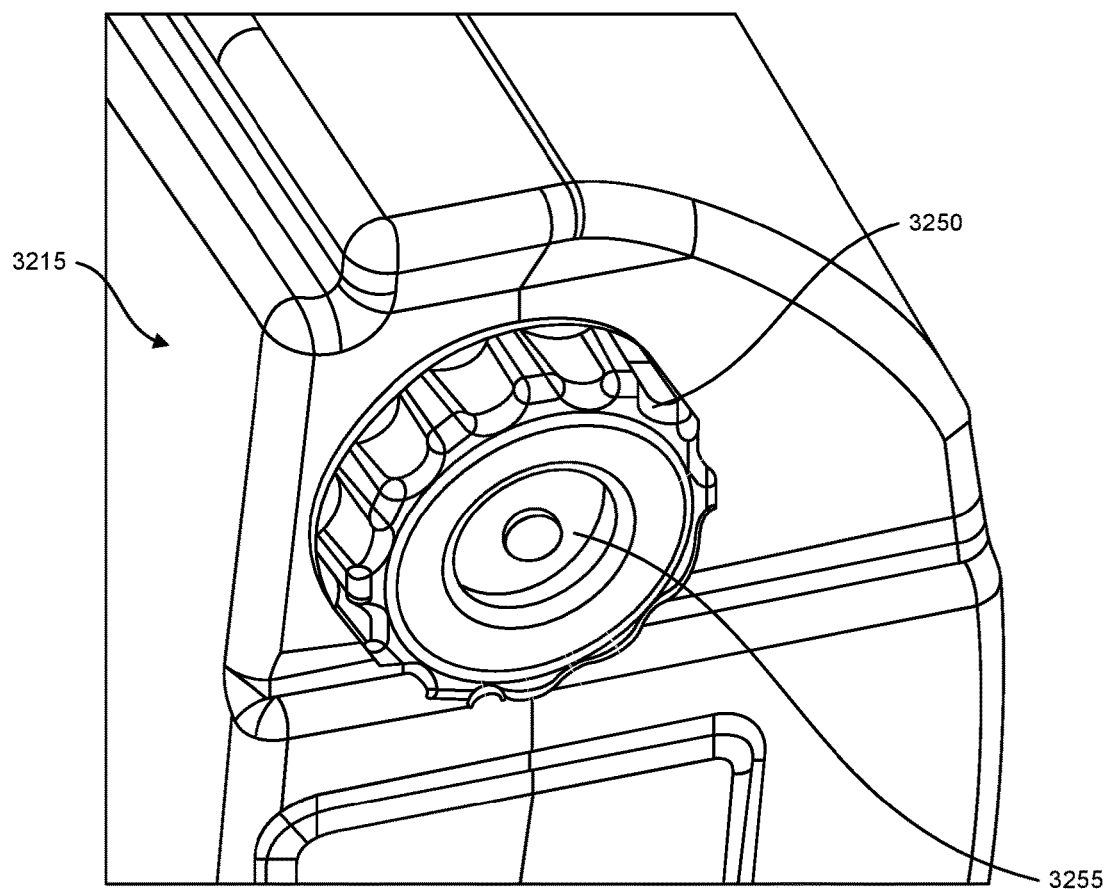
FIG. 32B shows an enlarged view of a bottom portion of the tank showing a valve assembly.

FIG. 32B shows an enlarged view of a bottom portion of the tank showing the valve assembly 3215. The valve assembly includes a valve cap 3250 that surrounds a pin valve 3255. As described in detail below, the pin valve 3255 transitions between a closed position that prevents fluid flow into and out of the tank, and an open position that permits fluid flow from the tank to the base. The pin valve 3255 has a default, closed state. The pin valve 3255 automatically transitions to the open state when the tank 3410 is properly seated within the base 3415.

The valve assembly between the base 2415 and the tank 2410 is mechanically configured such that a valved fluid passageway between the tank 2410 and the base 2415 automatically opens when the tank 2410 is properly seated in the base 2415.

Figure 33:
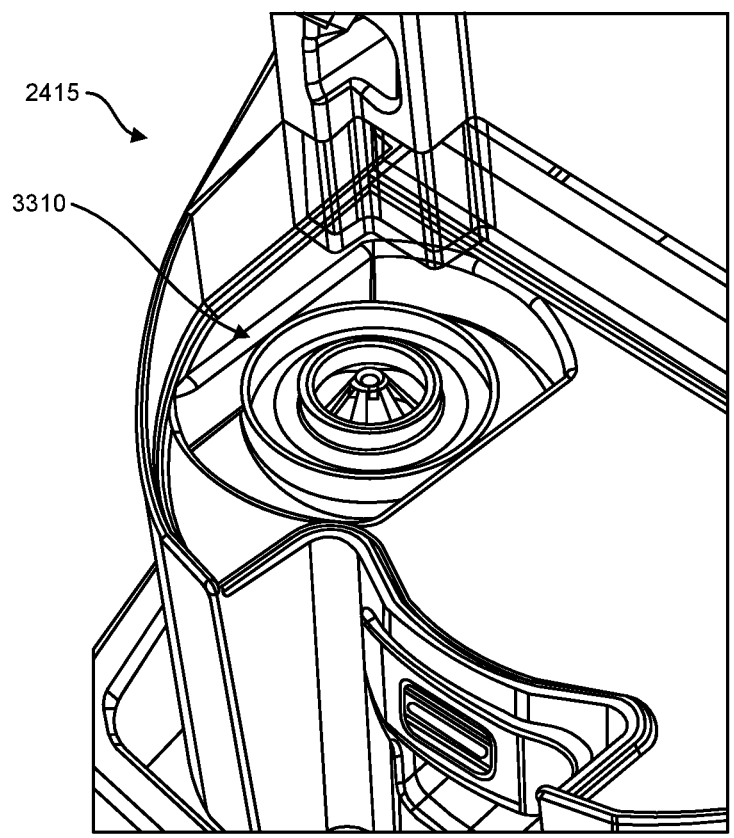
FIG. 33 shows an enlarged view of a portion of the base and shows a valve assembly of the base.

FIG. 33 shows an enlarged view of a portion of the base 2415 and shows a valve assembly 3310 of the base 2415. The valve assembly 3310 of the base 2415 is sized and shaped to mechanically interact with the valve assembly 3215 of the tank 2410. Specifically, the valve assembly 3215 of the tank 2410 couples with and/or seats within the valve assembly 3310 of the base 2410. When properly seated, the two valve assemblies interact such that the valve assembly 3215 of the tank automatically opens when the tank is properly seated in the base.

Figure 34:
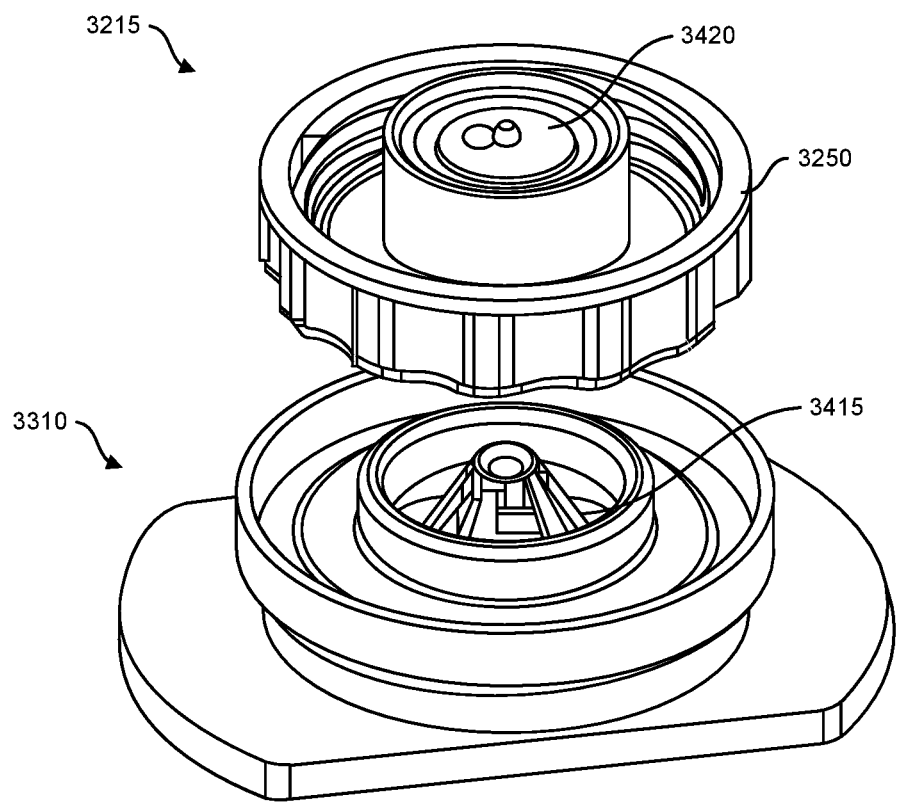
FIG. 34 shows a perspective view of the combined valve assemblies of the tank and the base.
Figure 35:
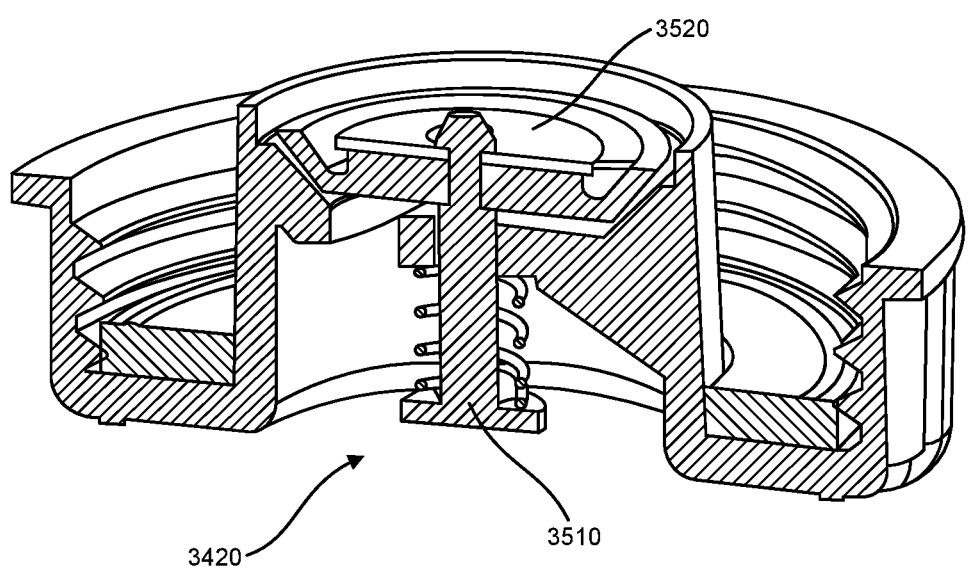
FIG. 35 shows a cross-sectional, perspective view of the combined valve assembly.

FIG. 34 shows a perspective view of the combined valve assemblies of the tank and the base. FIG. 35 shows a cross-sectional, perspective view of the combined valve assembly. With reference to FIG. 34, the valve assembly 3215 of the tank includes the one way valve cap 3250, which partially surrounds a spring valve 3420 that is closed in a default state. The valve assembly 3310 of the base 2415 includes a filter 3415 for filtering fluid that passes through the valve.

With reference to FIG. 35, the spring valve 3420 includes a valve pin 3510 that has an upper region that seats on a plate 3520. The spring valve 3420 includes a spring that biases the spring valve 3420 toward the closed position. When the valve assembly of the tank is seated within the valve assembly of the base, the spring valve 3420 is pushed by the interaction toward an open position so that fluid can flow from the tank into the base and toward the sprayer.

Figures 25A, 25B:
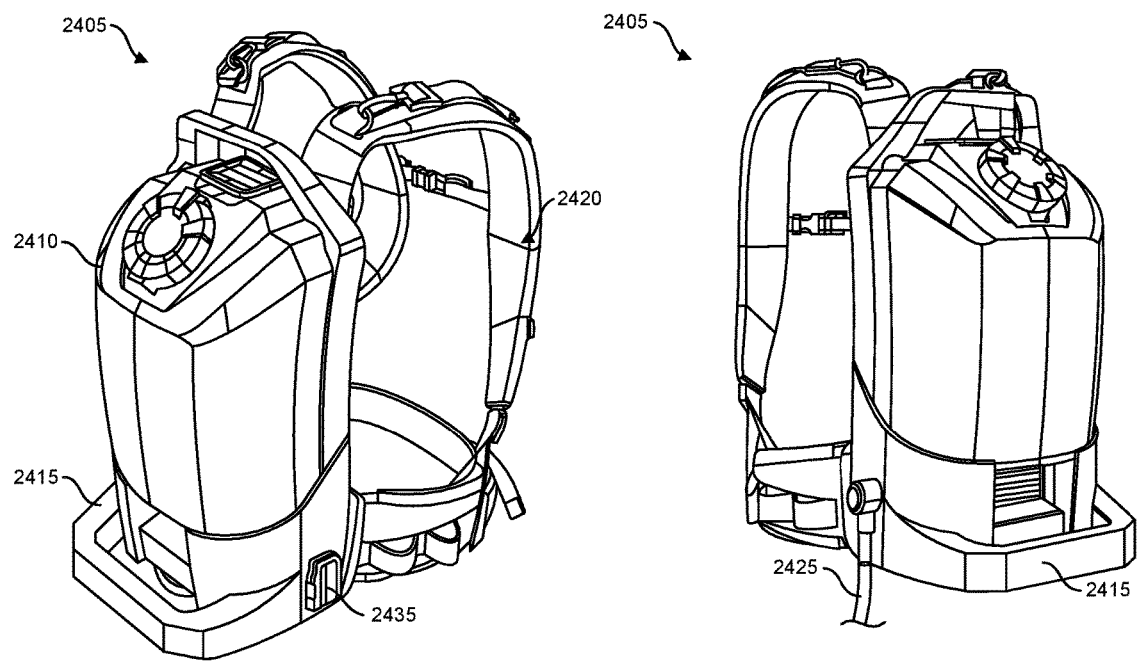
Figure 26:
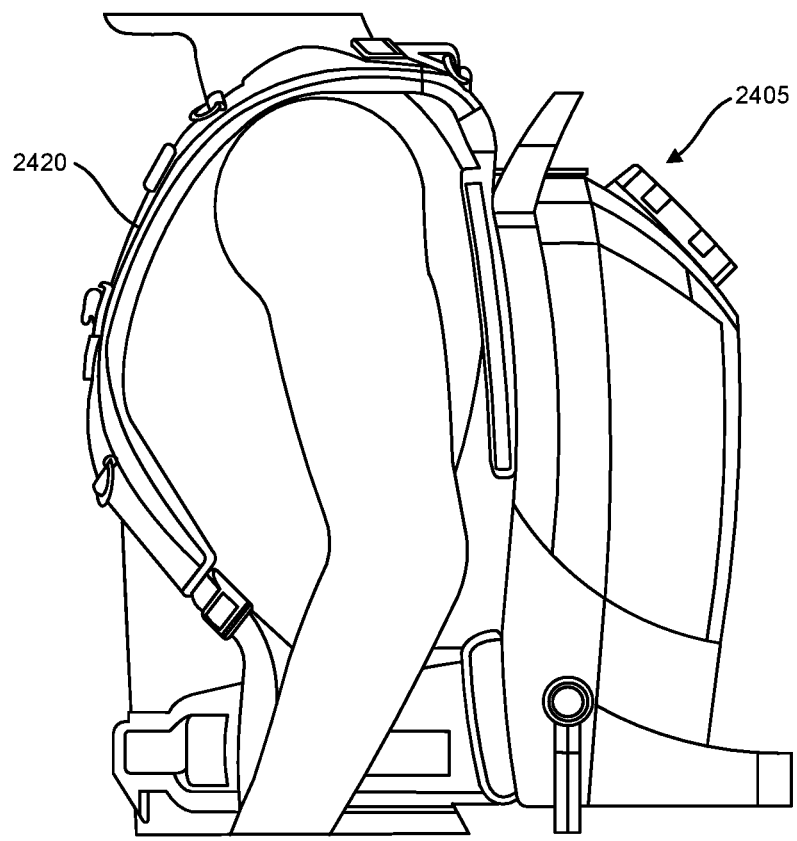
Figure 27:
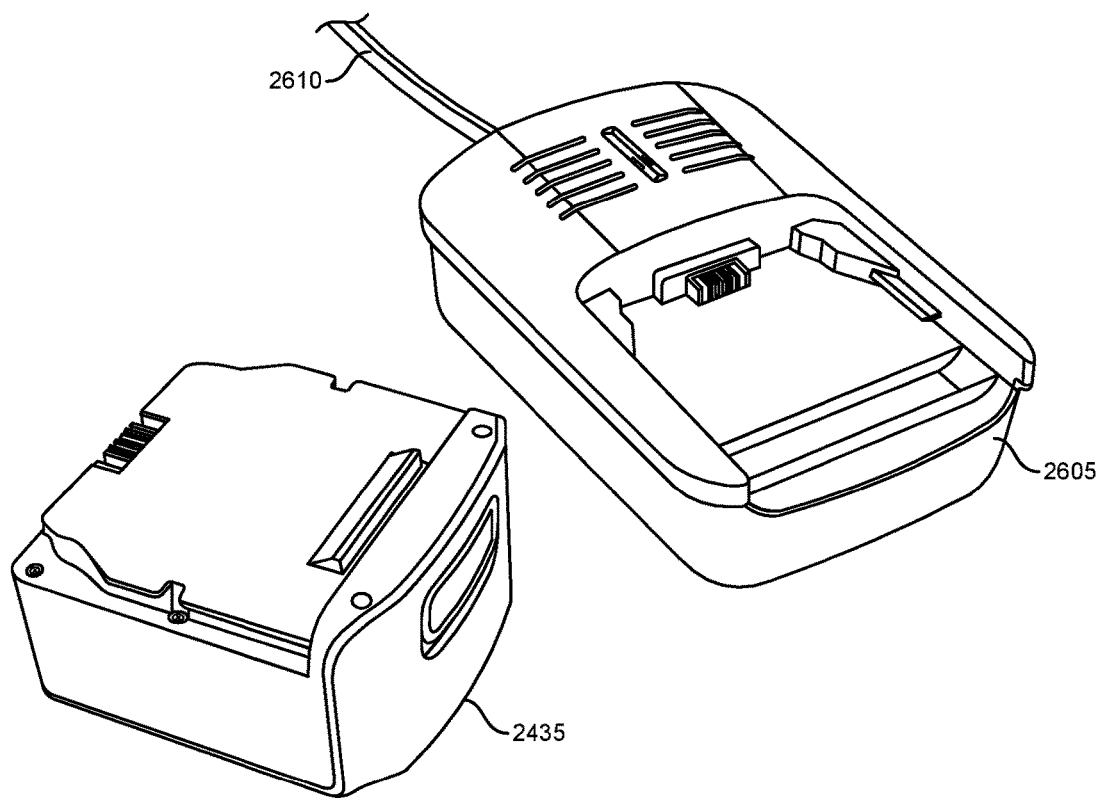
FIG. 27 shows the battery system of the backpack system.
Figure 36:
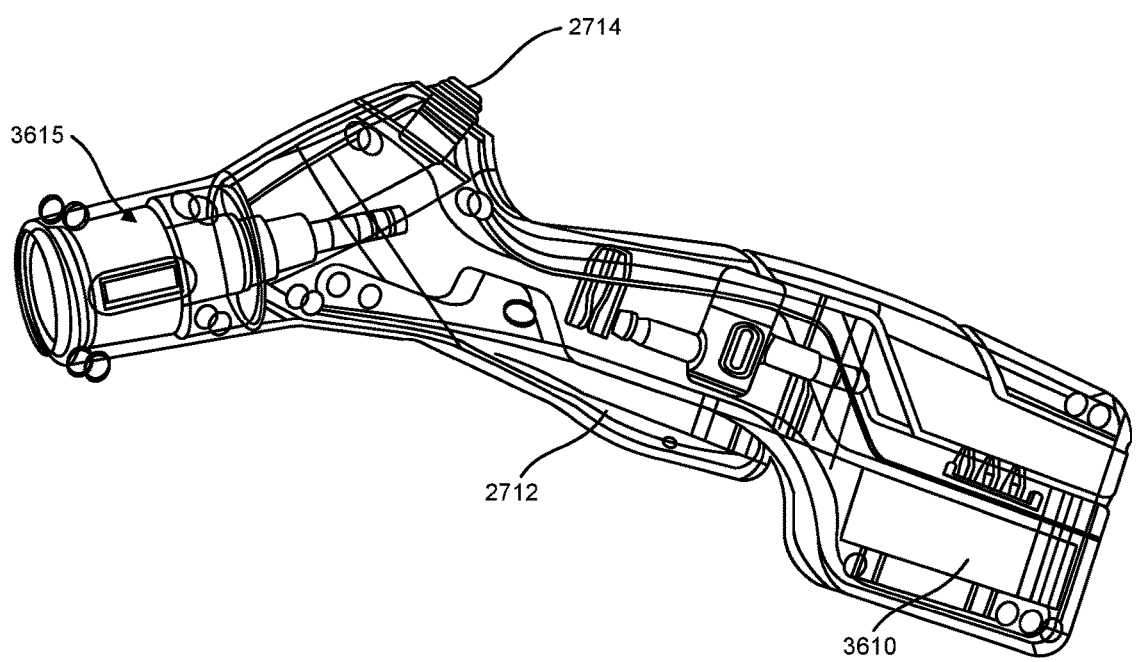
FIG. 36 shows a perspective view of the sprayer assembly with an outer housing of the sprayer assembly being partially transparent.

FIG. 36 shows a perspective view of the sprayer assembly with an outer housing of the sprayer assembly being partially transparent. As discussed above, the sprayer assembly is formed of an outer housing that has an ergonomic shape. A nozzle assembly 3615 is positioned within the outer housing in fluid communication with the tubing 2425 (FIG. 25) that is fluidly coupled to the fluid in the tank 2410. The outer housing includes one or more internal tubular members that provide a passageway for fluid to flow to the nozzle assembly 3615.

The sprayer assembly also includes an internal pump 3610 that causes a pressure differential to cause fluid to flow from the tank, through the tubing 2425, and into the nozzle assembly 3615 of the sprayer assembly. As mentioned, the sprayer assembly includes a first actuator 2712 that can be actuated by a user to activate the pump 3610. The sprayer assembly also includes a second actuator 2714, such as a button, that activates the electrostatic module of the device.

Figure 37:
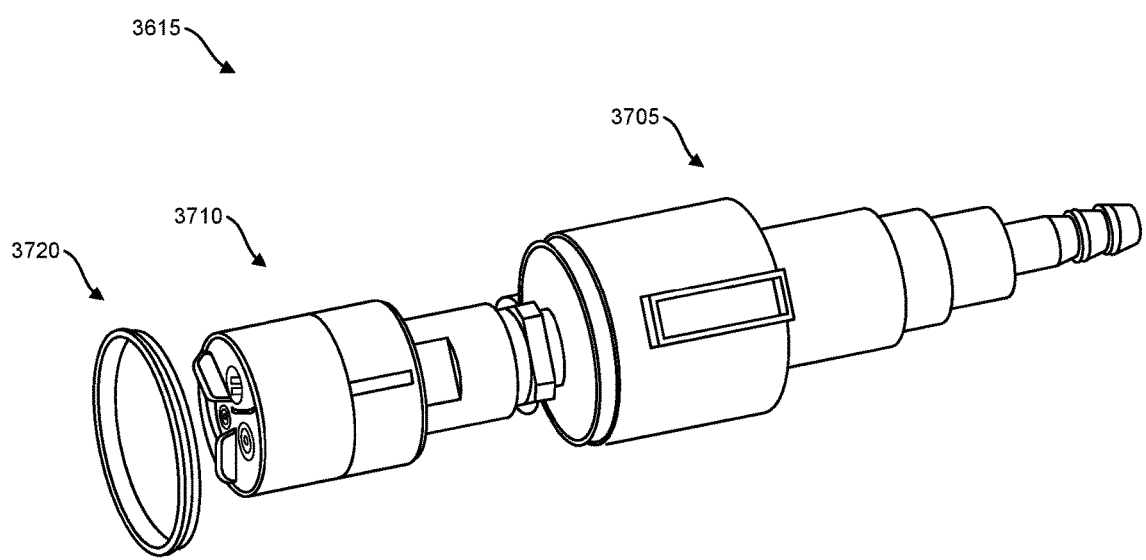
FIG. 37 shows a perspective, exploded view of the nozzle assembly.
Figure 38:
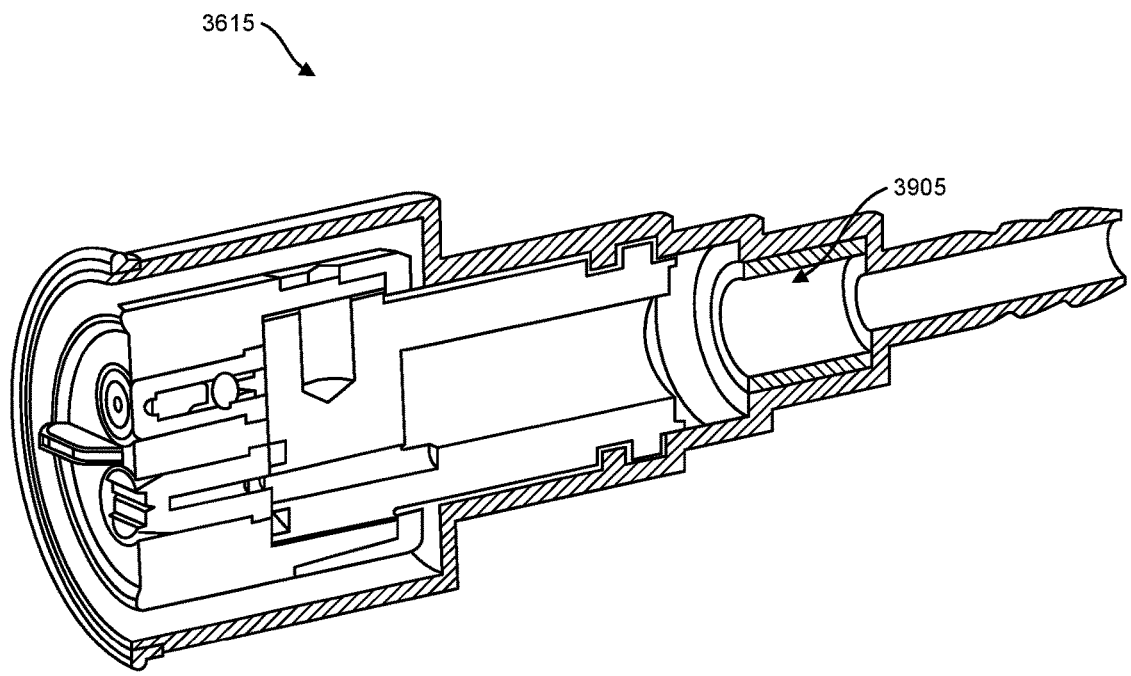
FIG. 38 shows a perspective, cross-sectional view of the nozzle assembly in an assembled state.
Figure 39:
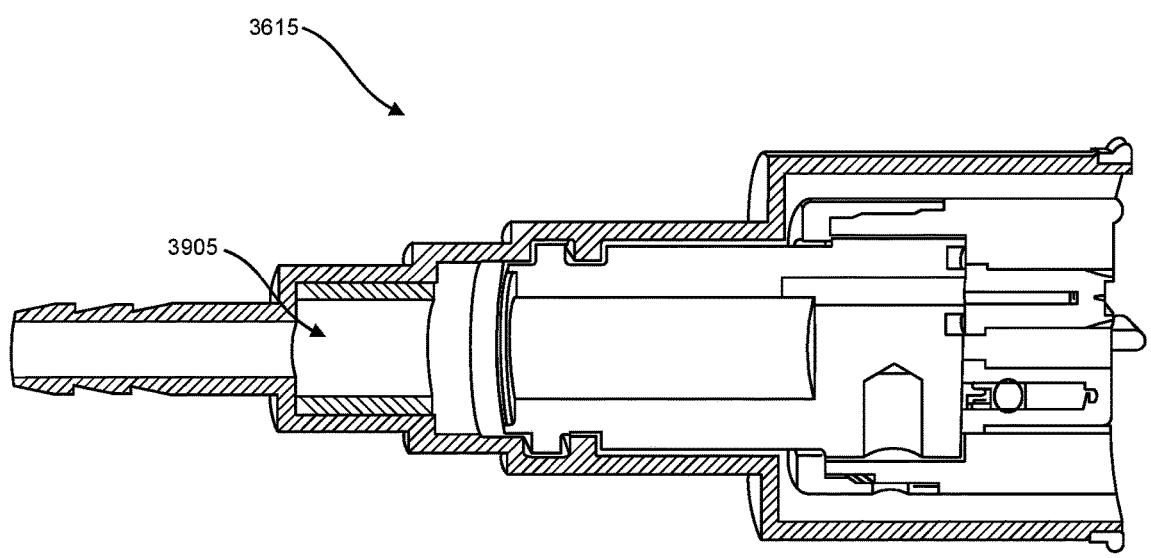
FIG. 39 shows a side, cross-sectional view of the nozzle assembly in an assembled state.
Figure 40:
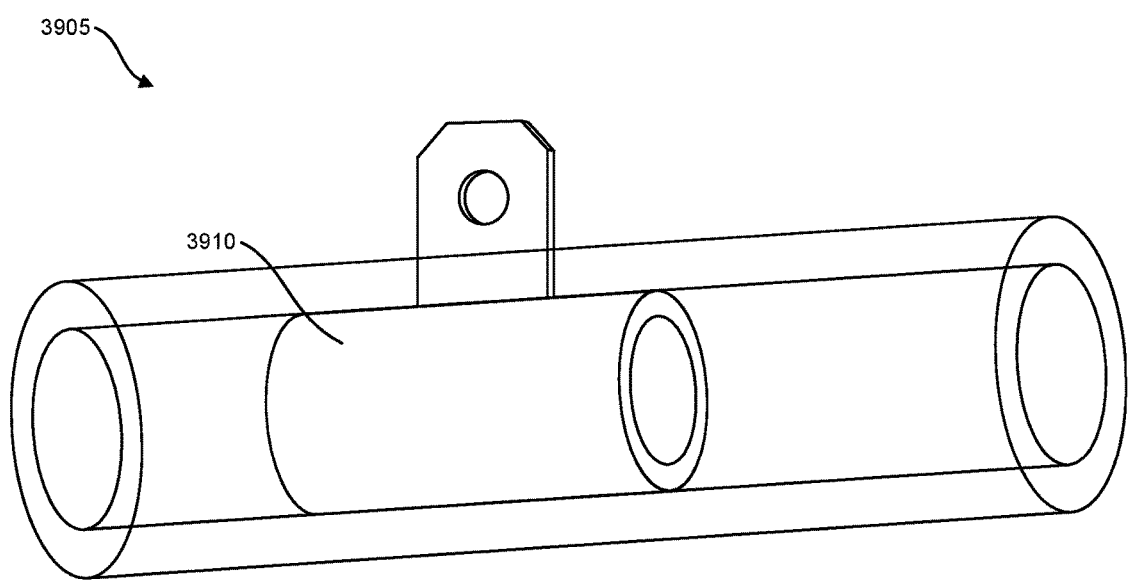
FIG. 40 shows a perspective, cross-sectional view of an ion tube isolator.
Figure 41:
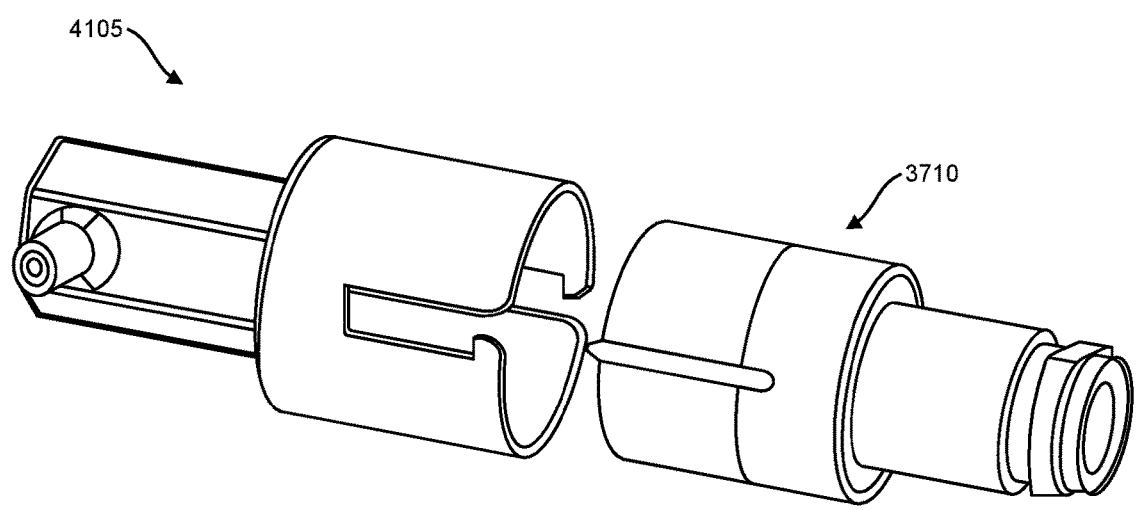
FIG. 41 shows a perspective view of a nozzle tool that removably and mechanically couples to the nozzle assembly for manipulating the nozzle component.

FIG. 37 shows a perspective, exploded view of the nozzle assembly 3615. FIG. 38 shows a perspective, cross-sectional view of the nozzle assembly in an assembled state. FIG. 39 shows a side, cross-sectional view of the nozzle assembly in an assembled state. The nozzle assembly 3615 can optionally be configured in a similar manner to the nozzle assembly of any of the other embodiments disclosed herein. In the embodiment of FIG. 38, the nozzle assembly includes a nozzle housing 3705 having an internal cavity that removably contains a nozzle holder or nozzle component 3710 in which one or more nozzles are positioned in a manner similar to the previous embodiment. An annular electrostatic ring 3720 is mounted on a forward edge of the nozzle housing 3705. The electrostatic ring 3720 forms an opening through which fluid is expelled from the tank/reservoir and through at least one of the nozzles by virtue of the pump creating a pressure differential. An insulator element, such as a rubber ring can be positioned on the electrostatic ring to electrically shield it from the outer housing of the sprayer.

There is a metal contact on the high voltage electrostatic ring that is exposed at a rear part of the electrostatic ring. A high voltage wire from the electrostatic module is soldered or otherwise electrically connected to this metal contact. The soldering point and adjacent exposed metal is completely sealed by epoxy or other insulator to avoid oxidation and leakage of ions from the electrodes. A ground wire from electrostatic module is connected to ground plate. As discussed, the ground wire is embedded in the handle of the sprayer so that it is in contact with the operator during operation. This serves as electrical return loop to complete an electrical circuit. The electrostatic ring is electrically charged so that it transfers the charge to the electrodes that are electrically connected to the ring. In another embodiment, the electrodes themselves are individually connected to the electrostatic module.

A one-way check valve can be positioned inside the nozzle assembly 3615 such that fluid must flow through the one way valve in order to flow out of the nozzle assembly. When the trigger that powers the fan is released by a user, the check valve closes and prohibits fluid from exiting the nozzle assembly when the trigger is released by the user. In this manner, residual fluid is prohibited from being released out of the system and onto the ground when the system is not in use.

An ion tube isolator 3905 is mounted within the nozzle assembly of the sprayer. FIG. 40 shows a perspective, cross-sectional view of the ion tube isolator 3905. The ion tube isolator 3905 functions a manner similar to the ion tube isolator described above with respect to the previous embodiment. The ion tube isolator 3905 electrically charges fluid flowing from the tank or pump and toward the nozzles. The ion tube isolator includes a tube 3910 through which fluid passes as well as a high voltage electrode assembly or module that is electrically connected to the electrostatic module and that is made of a conductive material such as metal. The module can include a lead where it can be electrically connected to the electrostatic module such as via a conductive wire.

In an embodiment the module is a conductive material, such as metal. In an embodiment only the module is conductive and the remainder of the tube 3910 is non-conductive and/or is insulated from contact with any other part of the system. The module may also be surrounded by an insulator that insulates it from contact with any other part of the system. As fluid flows through the tube 3910, the module directly contacts the fluid as it flows and passes a charge to the fluid through direct contact with the fluid. In this way, the ion tube isolator 3905 electrostatically charges the fluid prior to the fluid passing through the nozzle.

FIG. 41 shows a perspective view of a nozzle tool 4105 that removably and mechanically couples to the nozzle assembly for manipulating the nozzle component 3710. The nozzle tool 4105 is sized and shaped to be inserted into a front opening in the nozzle housing 3705. When inserted into the nozzle housing 3705, the nozzle tool 4105 mechanically couples to the nozzle component 3710 in a manner that permits the nozzle tool 4105 to lock and/or move the nozzle component relative to the nozzle housing.

In an embodiment, the tool 4105 couples to and removes nozzle component by a counter clock turn and by pushing in until nozzle component decouples and can be removed. In this regard, pushing the nozzle component deeper into the housing using the tool causes a threaded portion of the nozzle component to engage a threaded nut or bolt of the housing that secures the nozzle component to the housing. The user can then unthread the nozzle tool and remove it from the housing.

The tool 4105 can also be used to adjust the three-way nozzle by turning it in a desired rotational direction. The user can select two or more different spray patterns by turning the nozzle component so that a desired nozzle fluidly couples to the reservoir. In this regard, a portion of the tool mechanically attaches to the nozzle component so that it can apply force to the nozzle component and rotate it until a desired nozzle is in a position that is fluidly coupled to a fluid stream from the reservoir. The system may include a mechanism, such as spring and ball, that provides a noise (such as a clicking sound) when a nozzle is in a position to spray fluid.

The nozzle tool 4105 is sized and shaped to be grasped by a user. It can include a coupler region that can be removably coupled to a drive device, such as a wrench, or grasped by a user. In an embodiment, the coupler region is hexagonal shaped so that it can be mechanically coupled to a wrench including a socket wrench. The nozzle tool includes a cavity or seat that is size and shaped to receive the outer portion of the nozzle component. For example, the seat can have a shape that complements and receives the shape of the nozzle component. The nozzle tool also includes at least one opening that interlocks with a complementary-shaped protrusion on the nozzle component.

FIG. 42A shows a perspective view of a pump housing of the system, which includes a pneumatic head. The pump housing is sized and shaped to receive the pump, which can be similar or the same as the pump the pump described above with respect to the previous embodiment. The pump housing 4210 includes a top and a bottom inlet opening 4220 and a top and a bottom outlet opening 4230. Valves are positioned in each of the top and bottom in the openings for a total for valves. Fluid flows into the pump to the inlet opening 4220 and out of the pump through the outlet opening 4230. In an embodiment, the pump is a rotary pump that includes a connecting rod and a diaphragm. The diaphragm is positioned or coupled within a top diaphragm opening 4235 and an aligned bottom diaphragm opening. The rotary motion of the motor turn into the swing of a connecting rod causes the diaphragm to move up and down relative to the diaphragm opening 4235. The process of downward movement of the diaphragm a pump cavity will suck fluid through the inlet opening 4220. Upward movement of the diaphragm presses fluid out of the outlet opening 4230 and towards the nozzles. The mechanical transmission parts and a pump cavity are isolated by the diaphragm. The diaphragm does not need oil for auxiliary lubricating during the process of transmission, extraction and compression of the fluid.

The diaphragms have two holes that are cut into a circle. The valves (which can be plastic, for example) have a seating position inside of a pneumatic gasket. A top and a bottom lid of the housing secures the rubber diaphragms like an o-ring. The rubber diaphragm, when properly inserted, makes a water tight seal when screwed down to a pneumatic head assembly of the housing.

The top and bottom reservoir outlet openings allow water to flow in and out of each channel. The valves are inserted into the rubber diaphragms. The two channels equalize the pressure when the pneumatic valves are opening and closing to provide continues motion of suction and pressure. The pneumatic head has multiple channels or openings thereby allowing water to flow through the top and the bottom by using applied force from a DC motor. The motor rotates with a bearing that spins on an oval axis inside of the cam housing causing a up and down motion and side to side motion. The rubber diaphragm can be of a harder and thicker material which will act as a trampoline when the cam housing is attached to both sides of the diaphragm. The diaphragms move up and down generating an internal pressure. The valves will open and close allowing water pressure to circulate in in and out causing the system to be under a constant suction and flow pressure. The pressure is regulated and is equal to the suction pressure. The pressure can be adjusted by the thickness of the diaphragms and the rpm of the motor.

The cam has an oval shape allowing the bearing to be off-set to allow the cam to rotate up and down or side to side causing the rubber diaphragms to be pushed up and down. This causes an up and down motion on the pneumatic diaphragm, which in turn causes suction on one side of the pneumatic housing and pressure on the other side of the housing. As the water flows through the valve opening and closing the valves, the water is equal to both pressures. The one side of the pump draws in water while the other side pushes the water.

There are three bearings that are included in the pneumatic pump including a DC motor casing bearing. The first bearing is located inside of the DC motor housing to allow the shaft to spin freely when the motor is spinning at high speeds. The second bearing is located in the cam housing which is the pneumatic housing. All three bearings can be stainless steel, for example, and have stainless steel casing which allows the bearing not to overheat or rust. The third bearing is configured to keep the shaft and the cam aligned with the internal pneumatic head. This allows the inner motor bearing to stay aligned with the second cam shaft bearing and third bearing which keeps the shaft straight and true allowing the shaft to take more impact when spinning at high RPMs.

The four valves sit flush on the outside of the pneumatic housing, which are located in front of the inlet and outlet ports. The valves' purpose is to open and close such as on the order of 3000 times a minute. As this occurs, the diaphragm is pushed up and down by way of the bearing rotating inside the cam which rides freely between both pneumatic rubber diaphragms. The top and bottom diaphragm are a mirror image in size and in length. The cam attaches by two posts that connect them together. The cam rides freely between the two diaphragms making them independent and free to move in the direction of the bearing that is off-set allowing the cam to move in a direction up and down or side to side.

As mentioned, there are four rubber valves that open and close. The valves have different functions. The valves are meant to open and close allowing for water pressure or suctioning pressure to be continuous. One of the valves is always in a closed position so as not allowing water to back flow to the water pressure side. The opposing side of the valve allows suction pressure. A spoke check valve is in an open position and allows water pressure to flow when in one position. The pump has a suction side and a pressure side. The valves are Identical in the pneumatic housing. The cam moves the pneumatic diaphragm in a up and down motion causing the valves to open and close allowing water to be extracted from a reservoir and pushed out of the opposing side.

Figure 42A:
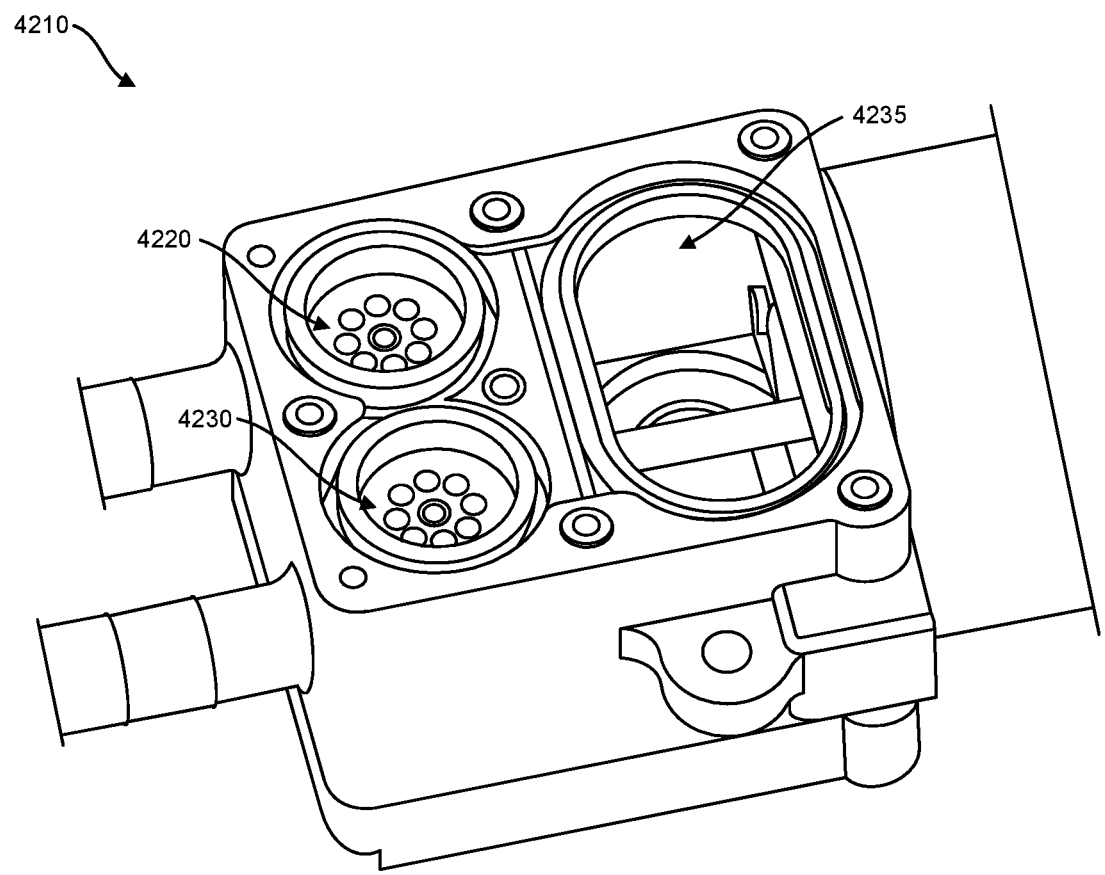
FIG. 42A shows a perspective view of an example pump housing of the system.
Figure 42B:
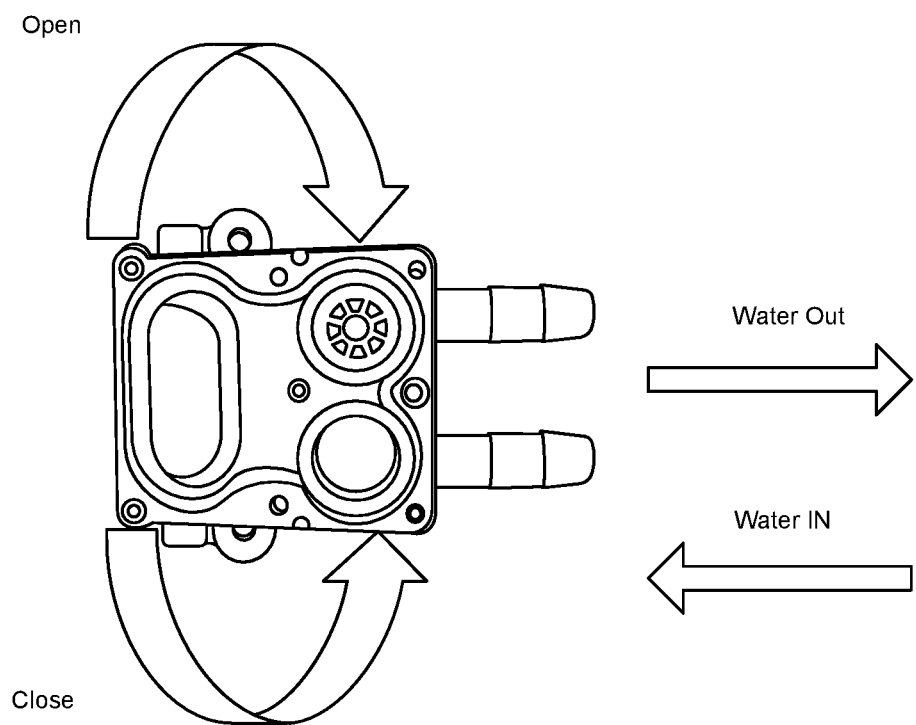
FIG. 42B illustrates pumping process.

FIG. 42B illustrates pumping process. The pump includes a collection of valves, which alternately and sequentially open and close allowing for water pressure or suctioning pressure to be continuous through the pump. A first valve is always in a closed position so that it prohibits fluid (e.g., water) to back flow to the water pressure side of the pump. A second, opposing side of the valve is configured to open and allow suction pressure. A third valve is in an open position and allows water pressure to flow. As mentioned, the pump has a suction side and a pressure side. A cam assembly inside the pump moves the pneumatic diaphragm in an up and down motion causing the valves to open and close allowing water to be extracted from the reservoir and pushed out of the opposing side. As the first valve and second valve open and close, the opening and closing of the valves alternately forms an opening and closing electrical circuit that exposes water in the tank to the electrostatic charger. This provides an electrical charge to the water the tank as described herein.

Figure 43:
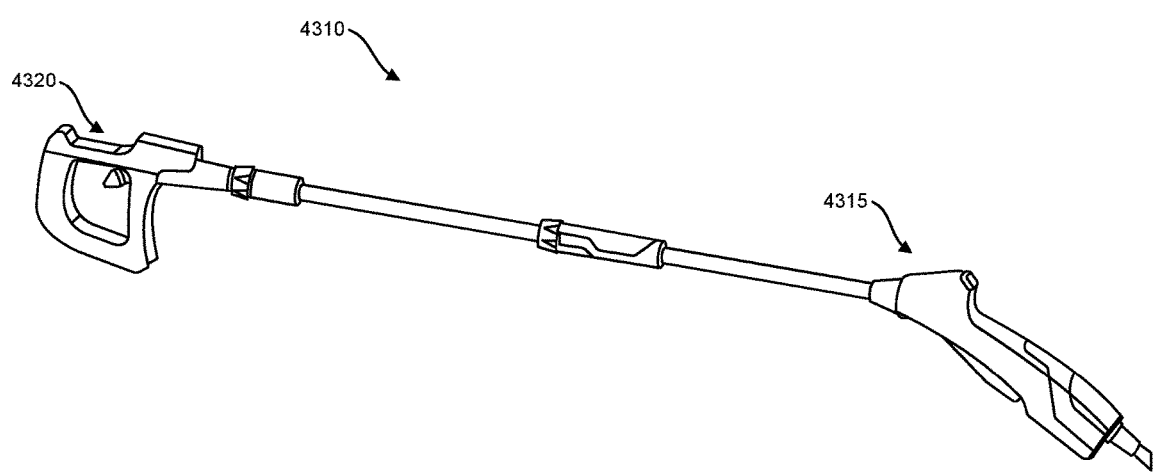
FIG. 43 shows another embodiment of a sprayer system.

FIG. 43 shows another embodiment of a backpack system. This embodiment of the backpack system includes an elongated wand 4310 that extends outward from a handle 4315 of the system. The wand 4310 can be sized and shaped to space the nozzle 4320 from the handle 4315, such as to enable a user to reach regions that are spaced apart from the handle 4315.

Figure 9:
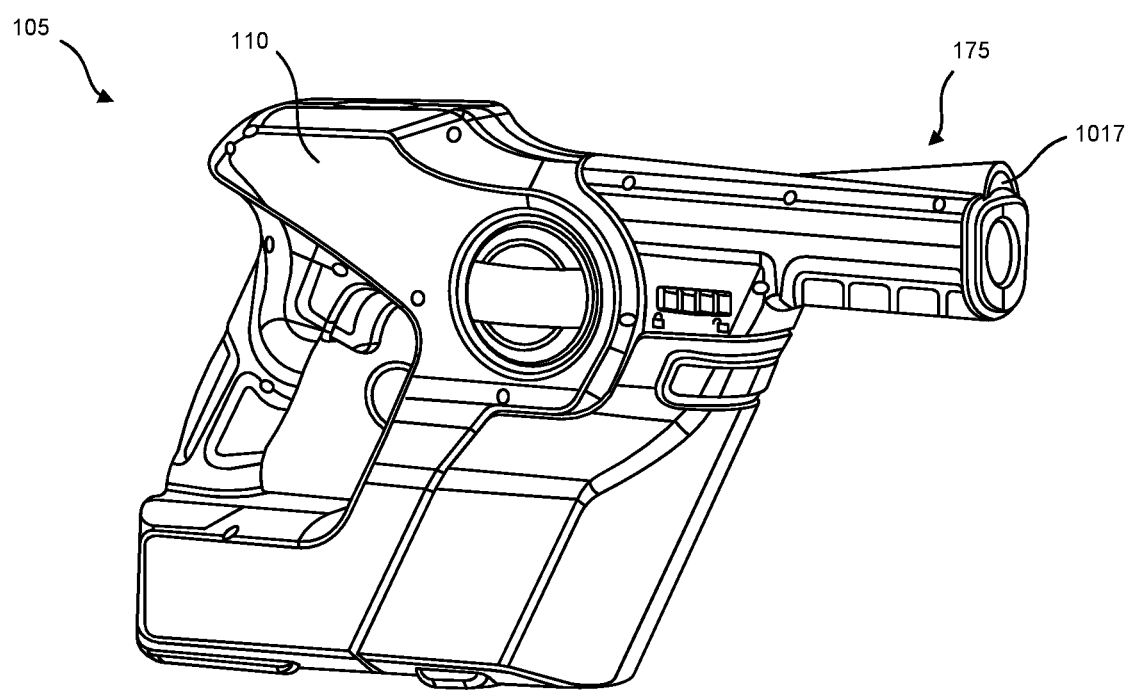
Figure 10:
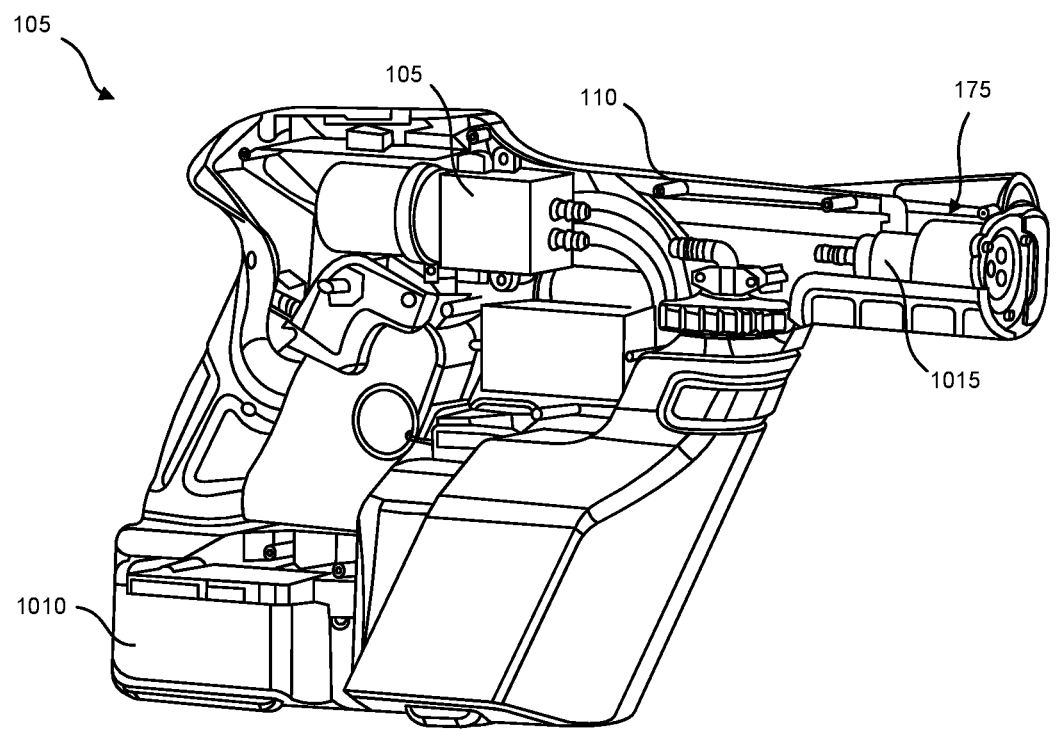
Figure 11:
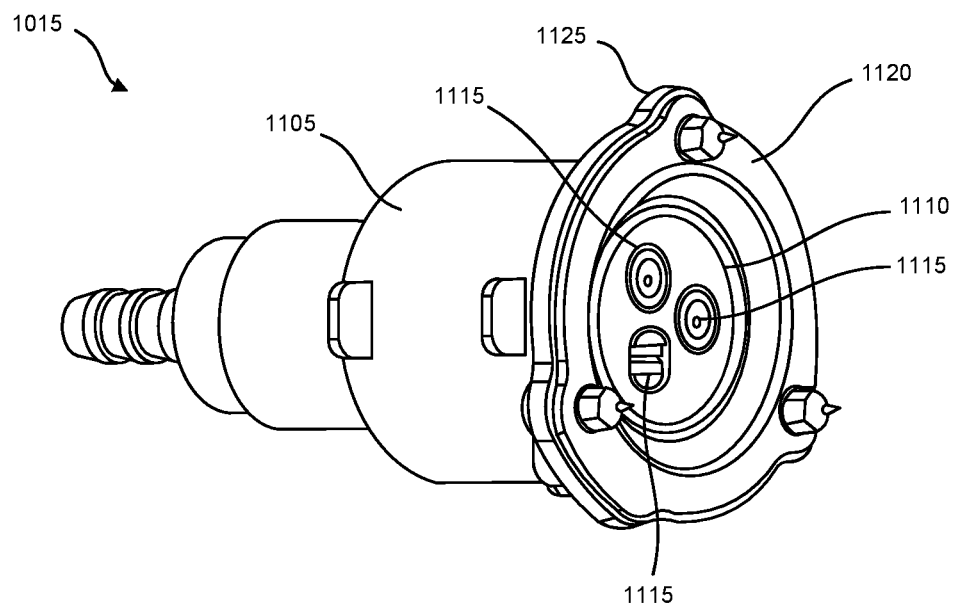
Figure 45:
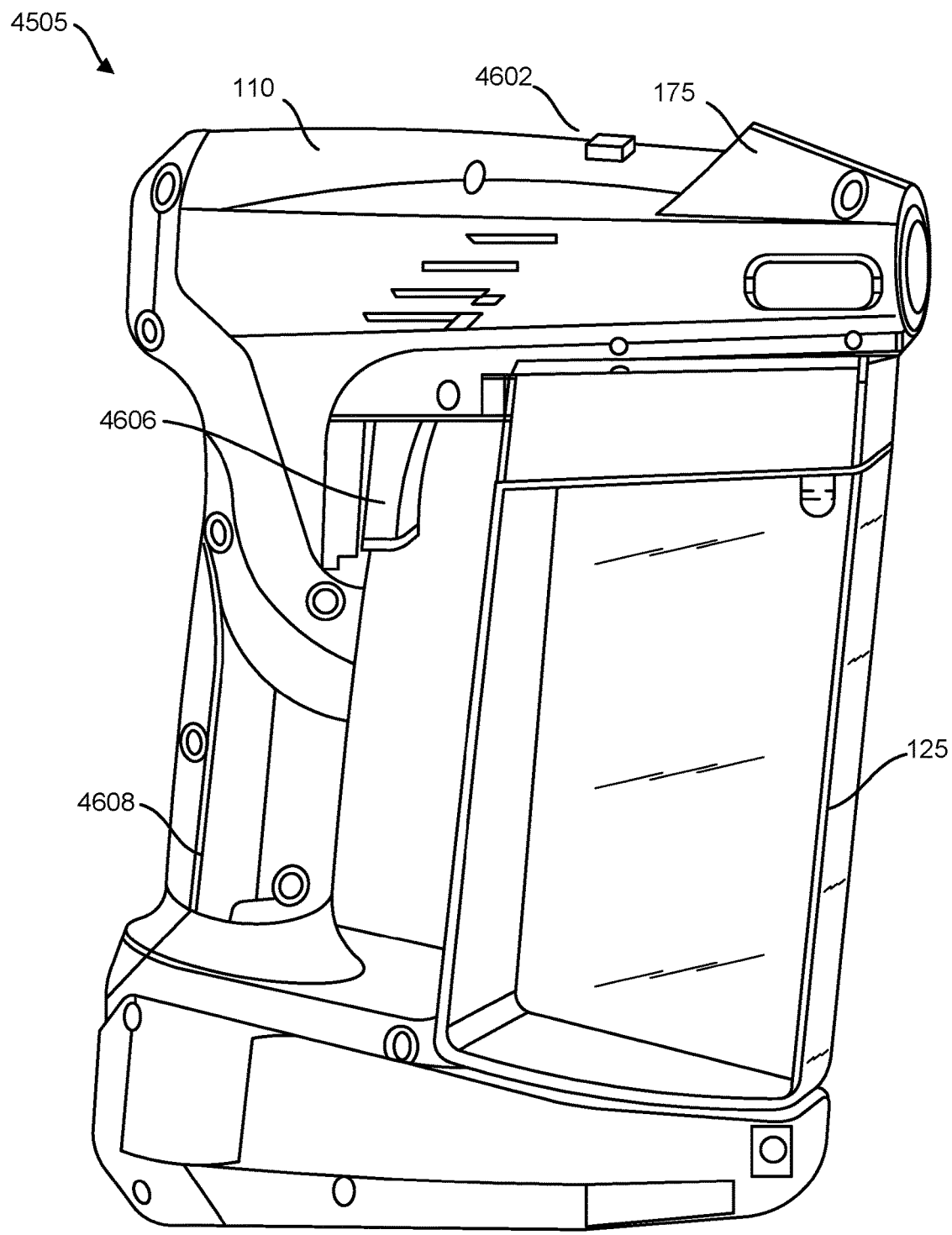
FIG. 45 shows a perspective view of another embodiment of a sprayer system.

FIG. 45 shows a perspective view of another embodiment of a sprayer system 4505, which is similar but smaller in size to the embodiment of FIG. 9. The system 4505 has an outer housing 110 that forms a handle 4608 that can ergonomically be grasped by a single hand of a user. The sprayer handle is ergonomically designed to fit all hand sizes. A ground wire or other structure can be embedded into the handle, as discussed with respect to the previous embodiments. The ground wire is positioned so that it will electrically contact the user's hand when the user grasps handle during use of the device. In an embodiment, the ground wire is made of copper and is a copper strip of material that contacts the user's hand when the user grasps the device although other materials, such as stainless steel, may be used.

The system 4505 includes at least one actuator, such as a trigger 4606, that can be actuated to turn on and also turn off an internal pump, as well as a second actuator, such as button 4602, for turning on and off an electrostatic charger for expelling a plume of electrostatically charged fluid from a fluid expelling region 175 of the system 105. The system 4505 has a removable tank or reservoir 125 for storing fluid to be expelled. There is sufficient space clearance between the reservoir 125 and the handle 4608 for a comfortable fit for the user when the user grasps the handle 4608. In an embodiment, when fully loaded with liquid the sprayer system weighs no more than 3 pounds although the weight can vary. In an embodiment, the reservoir 125 can contain up to half a liter of fluid although this can also vary.

The system 105 ejects high voltage ions to the air by means of a plurality of (such as three or more) detachable, high voltage ion discharge electrodes or pins of a predetermined spacing from each other on a rim of a nozzle holder (which can be as described above with reference to FIG. 14). The system can include a nozzle assembly such as any of the assemblies described herein. The high voltage ion discharge electrodes are each positioned along an axis that is in parallel to an axis of a spray nozzle so that the spray and ions are emitted in the same direction and along a parallel axis and therefore the droplets in the spray are surrounded and covered by ion stream and can be efficiently charged when they meet the ion stream. The electrodes thus emit, propel, or otherwise send out ions or charge in a direction parallel to the direct of fluid flow or an average direction of fluid flow from the nozzles.

Figure 46:
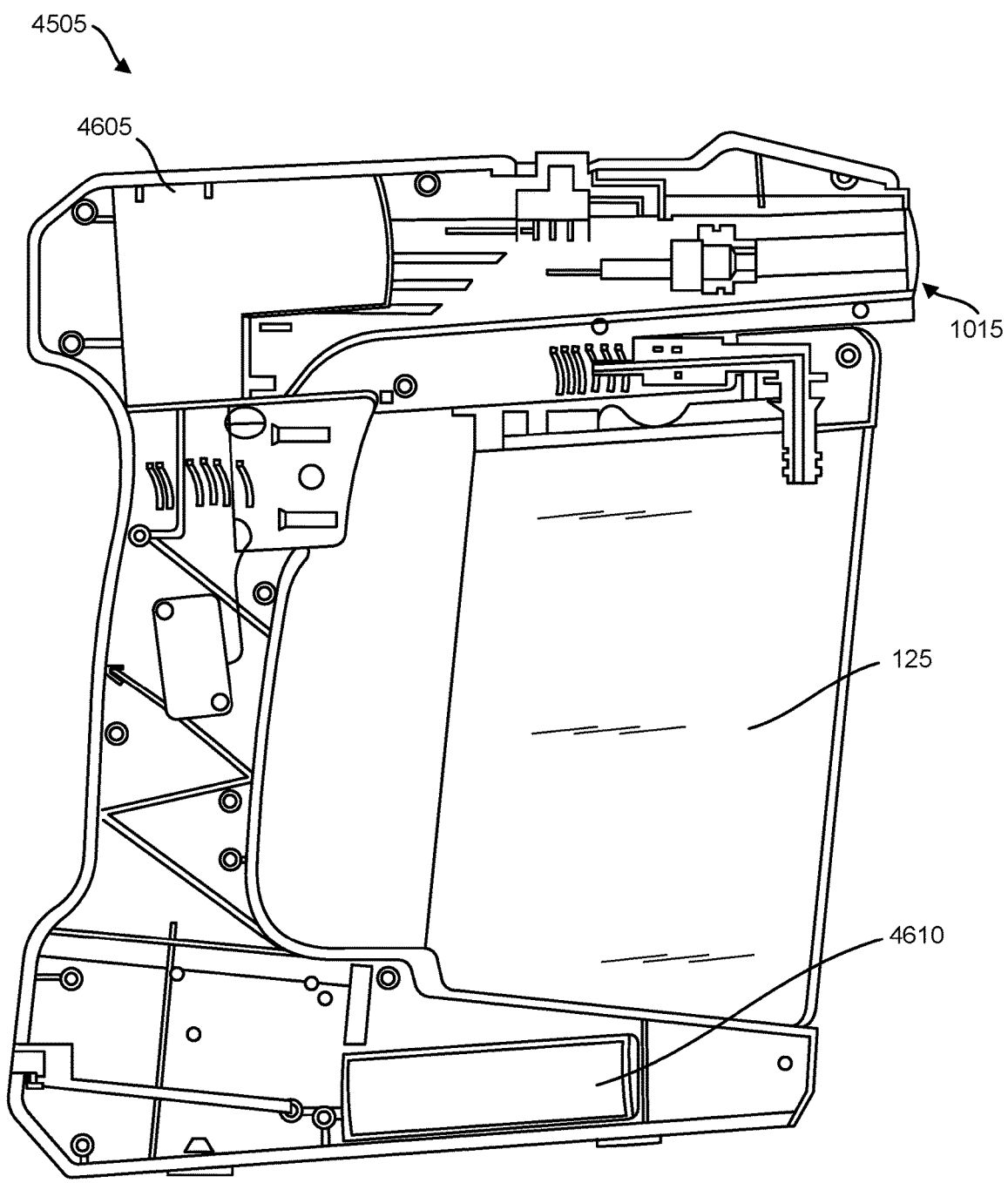
FIG. 46 shows the system of FIG. 45 with a portion of the outer housing removed to show internal components of the system.

FIG. 46 shows the system 4505 with a portion of the outer housing 110 removed to show internal components of the system 4505. The system 4505 includes a pump 4605 that is powered by a battery 4610, which can be rechargeable. The pump 4605 can be configured according to any of the embodiments of the pumps described herein, such as shown in FIG. 42A and related figures. The pump 4605 is fluidly coupled to fluid within the reservoir 125 such that the pump can cause a pressure differential to draw fluid from the reservoir and into a nozzle assembly 1015, which can be configured as described above in the previous embodiment. The system 105 further includes an electrostatic module that is electrically connected to an electrostatic ring, as described above with respect to the previous embodiments. The electrostatic module in an example embodiment is a 12 kV electrostatic module and it is configured to electrostatically charge an item, such as the electrodes, ring, and/or tube described below. In another embodiment, the electrostatic module is a 7 kV electrostatic module.

Figure 47:
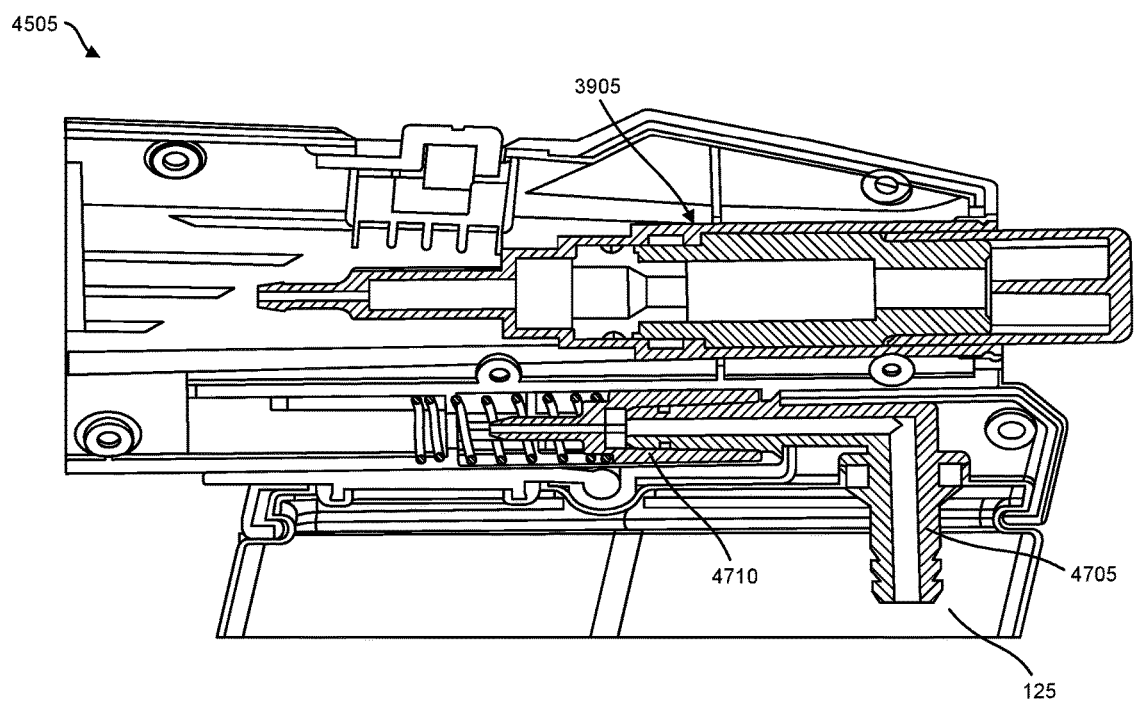
FIGS. 47 and 48 show cross-sectional views of the system in the region where the reservoir removably couples to the outer housing of the system.

As mentioned, the system 4505 has a removable reservoir 125 (such as a tank) for storing fluid to be expelled. FIG. 47 shows a cross-sectional view of the system 4505 in the region where the reservoir 125 removably couples (or otherwise attaches) to the outer housing 110 of the system. A top portion of the reservoir 125 mechanically attaches to the housing of the system. As described below, the reservoir and the housing coupled to one another in a secure and fluidly sealed male-female mechanical relationship.

In this regard, the system of 4505 includes a male member 4705 that has a first end positioned within the reservoir 125 and a second end positioned outside of the reservoir 125. The male member 4705 mechanically inserts into a female member 4710 in the housing when the reservoir 125 is attached to the outer housing 110. The male member 4705 has an internal lumen that communicates with a lumen within the housing and that ultimately lead to the nozzle assembly of the system and that also passes through the pump, such as the type of pump shown in FIG. 42A. In this manner, fluid can flow from the reservoir 125 to the nozzle assembly via the male member 4705 and the female member 4710 when the pump is activated.

Figure 48:
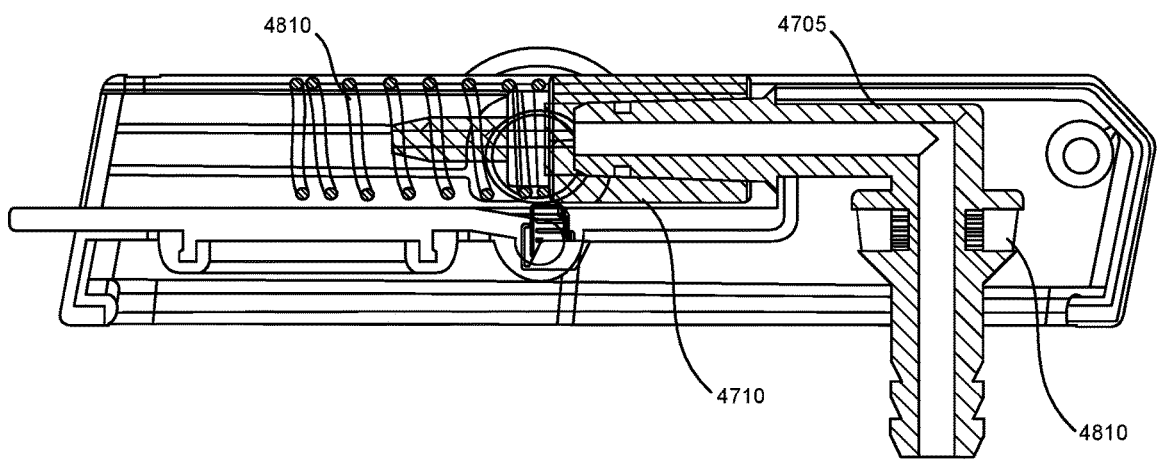

With reference to FIG. 47 and the enlarged view of FIG. 48, the male member 4705 can be an L-shaped structure, with a first, downwardly facing region that inserts into the reservoir 125, and a second, horizontal region that inserts into and sealingly mates with the female member 4710. The downwardly, vertical region includes can include or otherwise be attached to a tubing that reaches down to a bottom region of the reservoir 125. Such tubing provides a passageway for fluid to flow from the reservoir 1 by into the lumen of the male member 4705 when the pump is activated.

With reference to FIG. 48, and insulation or sealing member, such as an O-ring 4810, can be positioned on the male member 4705 to provide a seal between the male member and the structure in which it is mounted. This reduces the likelihood of liquid spilling out of the reservoir 125 if the device is toppled over. Any of the entryways into the reservoir 125 can include a filter to keep out contaminants.

When the reservoir 125 is attached to the outer housing 110 of the system, the male member 4705 sealingly mates with the female member 4710. As shown in the top-down view of FIG. 49, the system can include a locking member 4910, such as a pin, that secures or otherwise retains the male member 4705 inside the female member 4710 when the two are coupled. The locking member 4910 can be positioned between a locked state that secures the two members to one another and an unlocked state that permits the members to be released from one another. A biasing member, such as a spring 4810, can be positioned or otherwise coupled to the female member 4710. The spring 41 biases the male member 4705 outwardly from the female member 4710. This helps to disengage the male member of the female member when the lock member is unlocked, such as in a "quick release" fashion.

Figure 49:
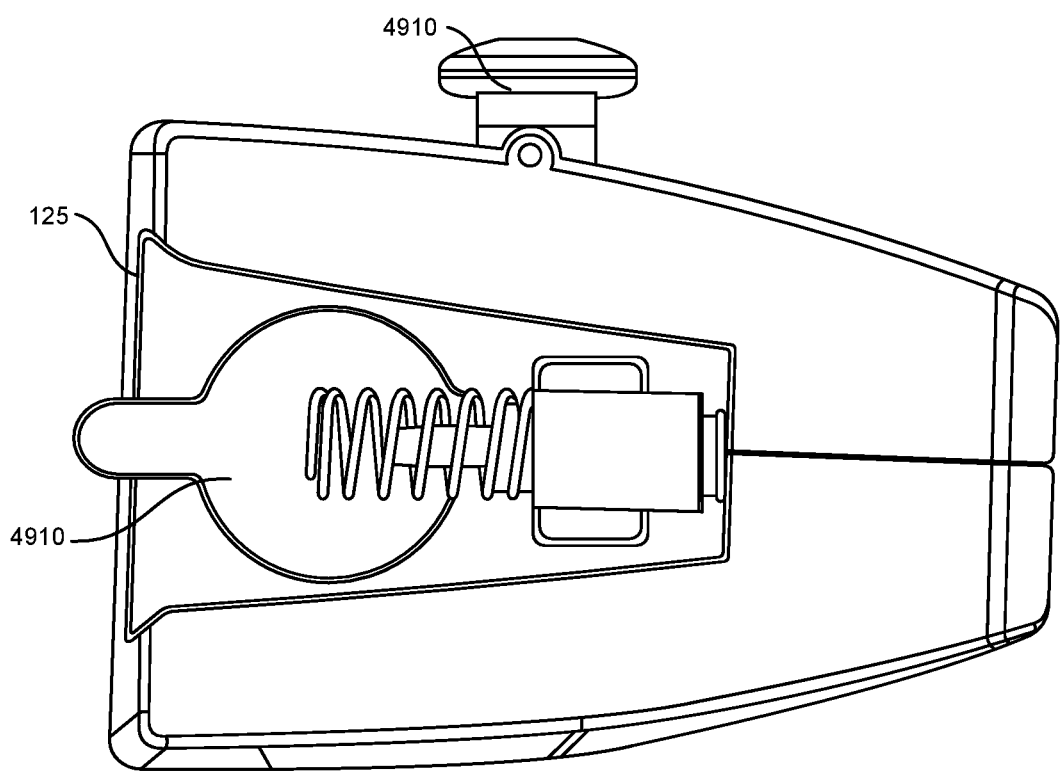
FIG. 49 shows a top-down of the system in the region where the reservoir removably couples to the outer housing of the system.

With reference to the top-down view of the reservoir 125 of FIG. 49, an upper region of the reservoir 125 includes an opening or spout that is covered by a cap 4920. The cap 4920 can move between a closed state wherein the 4920 sealingly covers the spout of the reservoir 125 and an open state wherein the cap 4910 does not cover the spout. When the spout is uncovered, a liquid can be poured into the reservoir 125. In an embodiment, the cap 4910 is secured to a top of the reservoir 125 in a hinged manner such that the cap 4910 can pivotably move between the open and closed position. The cap can have a beveled edge that seals with the reservoir such as in the manner of a sink stopper. In an embodiment, the cap is a 1 inch diameter cap.

With reference again to FIG. 47, the system 4505 includes an ion tube isolator 3905, which is mounted within the nozzle assembly of the sprayer. The ion tube isolator 3905 can be configured as described above respect to the previous embodiments. The electrostatic tube is isolated inside the nozzle housing, which acts as a protected barrier against an electrical shock when the nozzle has been insolated with electrostatic epoxy and over molded plastic. The electrostatic tube is electrically coupled to a wire. The wire is soldered into a small hole in the nozzle housing that allows the solder to attach the electrostatic ring of the nozzle assembly to a silicone wire. The silicone wire is then attached to the electrostatic module, which can be rated at 5 Kv to 7 Kv, for example. The nozzle assembly can also include a gasket, such as a double male sided gasket that allows the nozzle to keep a tight seal between the water nozzle and the electrostatic ring, both of which are inside the nozzle housing.

As discussed above, the nozzle assembly can include a one-way check valve, which prevents fluid from exiting the nozzle assembly when the user releases the trigger that powers the fan (i.e. the device is not being used). In this manner, residual fluid inside the device will not exit the system when the trigger is not being actuated by a user. It should be appreciated that any of the features described with respect to one embodiment described herein can be used with any of the other embodiments described herein.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

The invention claimed is:

1. An electrostatic sprayer device, comprising:
   a housing having a removable fluid reservoir, the fluid reservoir defining a cavity adapted to contain a fluid;
   at least one nozzle on the housing, the nozzle being fluidly connected to the reservoir via at least one fluid passageway, wherein the at least one nozzle emits fluid out of the housing in a direction along a flow pathway;

a pump in the housing coupled to the fluid reservoir, wherein the pump propels fluid from the reservoir to the at least one nozzle via the at least one fluid passageway, wherein the pump includes a diaphragm that moves relative to two channels inside the pump so as to propel fluid through the pump, the pump including at least one valve;

an electrostatic charging system that electrostatically charges the fluid, the electrostatic charging system being located entirely external of the reservoir such that the reservoir does not contain any component that effects electrostatic charging of fluid contained in the reservoir, the electrostatic charging system including an electrode assembly and an electrostatic module;

the electrode assembly system that electrostatically charges the fluid, wherein the electrode assembly system includes at least one of:

(1) a first electrode assembly formed of a plurality of electrodes positioned in a ring arrangement around the at least one nozzle and electrically attached to the electrostatic module, wherein each electrode emits ions along an axis that is parallel to the flow pathway of the fluid emitted from the at least one nozzle such that the plurality of electrodes form a static electrical field through which the fluid passes; and (2) a second electrode assembly formed of an electrically conductive tube that defines a portion of the at least one fluid passageway, wherein at least an electrically conductive portion of the tube is electrically coupled to the electrostatic module, and wherein the electrically conductive portion of the tube physically contacts the fluid as the fluid flows through the tube such that the electrically conductive portion applies an electrical charge to the fluid;

and wherein the electrostatic module is located external of the reservoir and also electrostatically charges the fluid inside the reservoir such that the fluid is electrostatically charged at both the reservoir and at the electrode assembly, wherein the electrostatic module electrostatically charges the fluid inside the reservoir from a location external to the reservoir by being exposed to the fluid in the tank via the pump as the at least one valve in the pump opens and closes;

a direct current battery inside the housing, wherein the battery powers at least one of the electrostatic module and the pump; and a cap on the reservoir, wherein the cap includes a duckbill valve that provides a vent for fluid to enter into the interior of the reservoir from atmosphere as the pump of the system pulls a vacuum in the reservoir.

2. The sprayer device as in claim 1, wherein the plurality of electrodes of the first electrode assembly are positioned on a ring through which the flow pathway passes and wherein the plurality of electrodes includes three electrodes spaced in 120-degree increments about the ring.

3. The sprayer device as in claim 1, wherein each electrode of the first electrode assembly is an elongated pin that extends along an electrode axis that is parallel with a direction along which the at least one nozzle emits fluid.

4. The sprayer device as in claim 1, wherein the at least one nozzle includes three nozzles.

5. The sprayer device as in claim 4, wherein each of the three nozzles are movable relative to the flow pathway so that a user can selectively couple a desired nozzle to the reservoir.

6. The sprayer device as in claim 1, wherein the at least one nozzle is positioned on a nozzle housing, and wherein the nozzle housing and the at least one nozzle is removable from the housing.

7. The sprayer device as in claim 6, further comprising a tool that can remove the nozzle housing.

8. The sprayer device as in claim 7, wherein the at least one nozzle includes three nozzles that are movable so that a user can selectively couple a desired nozzle to the reservoir, and wherein the tool can also move the nozzles.

9. The sprayer device as in claim 1, wherein the housing is sized and shaped to be held in a single hand of a user.

10. The sprayer device as in claim 9, wherein the housing includes a handle and a trigger that is actuated to active the device, and further comprising an electrical ground element embedded in the handle, the electrical ground element positioned so that the electrical ground element contacts a user's hand when a user grasps the handle.

11. The sprayer device as in claim 1, wherein each electrode of the first electrode assembly is an elongated pin, and further comprising an insulator that contacts and covers each pin such that only a tip of the pin is uninsulated.

12. The sprayer device as in claim 1, wherein the pump pulls a vacuum in the housing to cause fluid to flow from the reservoir to the at least one nozzle.

13. The sprayer device as in claim 1, wherein the duckbill valve allows positive and negative ions to enter the reservoir such that the reservoir is charged with positive and negative ions.

14. The electrostatic sprayer device of claim 1, wherein any component that effects electrostatic charging of fluid in the reservoir is located external to the reservoir.

15. A method of electrostatically spraying fluid, comprising:

providing a sprayer device, the sprayer device including:
 a housing having a removable fluid reservoir, the fluid reservoir containing a fluid;
 at least one nozzle on the housing, the nozzle being fluidly connected to the reservoir via at least one fluid passageway, wherein the at least one nozzles emits fluid out of the housing in a direction along a flow pathway;
a pump in the housing coupled to the fluid reservoir, wherein the pump propels fluid from the reservoir to the at least one nozzle via the at least one fluid passageway, wherein the pump includes a diaphragm that moves relative to two channels inside the pump so as to propel fluid through the pump, the pump including at least one valve;
an electrostatic charging system that electrostatically charges the fluid, the electrostatic charging system being located entirely external of the reservoir, the electrostatic charging system including an electrode assembly and an electrostatic module;
the electrode assembly system that electrostatically charges the fluid, wherein the electrode assembly system includes at least one of:
(1) a first electrode assembly formed of a plurality of electrodes positioned in a ring arrangement around the at least one nozzle and electrically attached to the electrostatic module, wherein each electrode emits ions along an axis that is parallel to the flow pathway of the fluid emitted from the at least one nozzle such that the plurality of electrodes form a static electrical field through which the fluid passes; and
(2) a second electrode assembly formed of an electrically conductive tube attached to the at least one fluid passageway, wherein at least an electrically conductive portion of the tube is electrically coupled to the electrostatic module, and wherein the electrically conductive portion of the tube physically contacts the fluid as the fluid flows through the tube such that the electrically conductive portion applies an electrical charge to the fluid;

and wherein the electrostatic module is located external of the reservoir and also electrostatically charges the fluid inside the reservoir such that the fluid is electrostatically charged at both the reservoir and at the electrode assembly, wherein the electrostatic module electrostatically charges the fluid inside the reservoir from a location external to the reservoir by being exposed to the fluid in the tank via the pump as the at least one valve in the pump opens and closes;

a direct current battery that powers at least one of the electrostatic module and the pump;

a cap on the reservoir, wherein the cap includes a duckbill valve that provides a vent for fluid to enter into the interior of the reservoir from atmosphere as the pump of the system pulls a vacuum in the reservoir; and electrostatically charging the fluid in the reservoir from a location external to the reservoir such that any component that effects electrostatic charging of fluid in the reservoir is located external to the reservoir;

causing the fluid in the reservoir to flow through the fluid passageway toward the at least one nozzle;

electrostatically charging the fluid as the fluid flows through the fluid passageway toward the at least one nozzle;

causing the fluid to spray out of the nozzle.

* * * * *